US009327010B2

(12) United States Patent
Ellis-Behnke et al.

(10) Patent No.: US 9,327,010 B2
(45) Date of Patent: May 3, 2016

(54) COMPOSITIONS AND METHODS FOR PROMOTING HEMOSTASIS AND OTHER PHYSIOLOGICAL ACTIVITIES

(75) Inventors: Rutledge Ellis-Behnke, Canton, MA (US); Shuguang Zhang, Lexington, MA (US); Gerald Schneider, Somerville, MA (US); Kwok-Fai So, Pokfulam (HK); David Tay, Pokfulam (HK); Yu-Xiang Liang, Pokfulam (HK)

(73) Assignees: Massachusetts Institute of Technology, Cambridge, MA (US); Versitech Limited, Hong Kong (HK)

( * ) Notice: Subject to any disclaimer, the term of this patent is extended or adjusted under 35 U.S.C. 154(b) by 0 days.

(21) Appl. No.: 11/411,745

(22) Filed: Apr. 25, 2006

(65) Prior Publication Data

US 2007/0203062 A1    Aug. 30, 2007

Related U.S. Application Data

(60) Provisional application No. 60/674,612, filed on Apr. 25, 2005, provisional application No. 60/758,827, filed on Jan. 13, 2006.

(51) Int. Cl.
*A61K 38/08*    (2006.01)
*A61K 9/00*    (2006.01)
*A61K 38/10*    (2006.01)

(52) U.S. Cl.
CPC .............. *A61K 38/08* (2013.01); *A61K 9/0019* (2013.01); *A61K 38/10* (2013.01)

(58) Field of Classification Search
None
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson et al. | |
| 4,272,398 A | 6/1981 | Jaffe | |
| 4,636,208 A | 1/1987 | Rath | |
| 4,829,000 A | 5/1989 | Kleinman et al. | |
| 4,861,627 A | 8/1989 | Mathiowitz et al. | |
| 5,019,646 A | 5/1991 | Furcht et al. | |
| 5,126,141 A | 6/1992 | Henry | |
| 5,180,375 A | 1/1993 | Feibus | |
| 5,192,302 A | 3/1993 | Kensey et al. | |
| 5,222,974 A | 6/1993 | Kensey et al. | |
| 5,645,565 A | 7/1997 | Rudd et al. | |
| 5,670,483 A | 9/1997 | Zhang et al. | |
| 5,955,343 A | 9/1999 | Holmes et al. | |
| 6,333,194 B1* | 12/2001 | Levy et al. .................... 435/450 |
| 6,368,877 B1 | 4/2002 | Zhang et al. | |
| 6,548,630 B1 | 4/2003 | Zhang et al. | |
| 6,663,655 B2 | 12/2003 | Ginn et al. | |
| 6,711,879 B2 | 3/2004 | Korteweg et al. | |
| 6,800,116 B2 | 10/2004 | Stevens et al. | |
| 6,800,481 B1 | 10/2004 | Holmes et al. | |
| 6,844,324 B1 | 1/2005 | Zhang et al. | |
| 6,953,656 B2 | 10/2005 | Jacobson et al. | |
| 6,953,659 B2 | 10/2005 | Jacobson et al. | |
| 7,098,028 B2 | 8/2006 | Holmes et al. | |
| 7,179,784 B2 | 2/2007 | Zhang et al. | |
| 7,449,180 B2 | 11/2008 | Kisiday et al. | |
| 7,846,891 B2 | 12/2010 | Ellis-Behnke et al. | |
| 8,021,570 B2 | 9/2011 | Gellman et al. | |
| 8,022,178 B2* | 9/2011 | Horii et al. .................... 530/324 |
| 9,084,837 B2 | 7/2015 | Ellis-Behnke et al. | |
| 2001/0024784 A1 | 9/2001 | Wagner | |
| 2002/0072074 A1 | 6/2002 | Zhang et al. | |
| 2002/0160471 A1 | 10/2002 | Kisiday et al. | |
| 2003/0008011 A1 | 1/2003 | Mershon | |
| 2003/0166846 A1 | 9/2003 | Rothstein et al. | |
| 2003/0176335 A1* | 9/2003 | Zhang et al. .................... 514/12 |
| 2004/0011201 A1 | 1/2004 | Stevens et al. | |
| 2004/0023414 A1 | 2/2004 | Zhang et al. | |
| 2004/0087013 A1 | 5/2004 | Holmes et al. | |
| 2004/0204561 A1 | 10/2004 | Ellison | |
| 2004/0242469 A1 | 12/2004 | Lee et al. | |
| 2005/0107289 A1 | 5/2005 | Ghadiri et al. | |
| 2005/0181973 A1 | 8/2005 | Genove et al. | |
| 2005/0287186 A1* | 12/2005 | Ellis-Behnke et al. ....... 424/423 |

(Continued)

FOREIGN PATENT DOCUMENTS

| | | |
|---|---|---|
| AU | 2006241123 | 11/2006 |
| GB | 1 006 606 A | 10/1965 |
| JP | 5-204646 | 8/1993 |
| JP | 09-506011 A | 6/1997 |
| JP | 2001-526561 A | 12/2001 |
| JP | 2005-074079 A | 3/2005 |
| JP | 2008-539257 A | 11/2008 |
| WO | WO-95/09659 A1 | 4/1995 |
| WO | WO 96/40033 A1 | 12/1996 |
| WO | WO 97/37694 A1 | 10/1997 |

(Continued)

OTHER PUBLICATIONS

Holmes et al., PNAS 2000, v97 pp. 6728-6733.*

(Continued)

*Primary Examiner* — Maury Audet
(74) *Attorney, Agent, or Firm* — Wolf, Greenfield & Sacks, P.C.

(57) ABSTRACT

Compositions that include nanoscale structured materials or precursors thereof (e.g., self-assembling peptides) are described. The compositions can include other substances (e.g., a vasoconstrictor). Also described are methods for using the compositions to promote hemostasis, to protect the skin or wounds from contamination, to decontaminate a site upon removal of previously applied compositions that provided a protective coating, and to inhibit the movement of bodily substances other than blood. The compositions are also useful in isolating tissue, removing tissue, preserving tissue (for, e.g., subsequent transplantation or reattachment), and as bulking, stabilizing or hydrating agents. Medical devices that include the compositions (e.g., a stent or catheter), bandages or other wound dressings, sutures, and kits that include the compositions are also described.

7 Claims, 2 Drawing Sheets

(56) References Cited

U.S. PATENT DOCUMENTS

| | | |
|---|---|---|
| 2006/0019309 A1 | 1/2006 | Zhang et al. |
| 2006/0025524 A1 | 2/2006 | Schneider et al. |
| 2006/0084607 A1* | 4/2006 | Spirio .................. A61K 9/0019 514/21.4 |
| 2006/0088510 A1 | 4/2006 | Lee et al. |
| 2006/0148703 A1 | 7/2006 | Lee et al. |
| 2006/0199778 A1 | 9/2006 | Ellis-Behnke et al. |
| 2006/0211615 A1 | 9/2006 | Zhang et al. |
| 2008/0032934 A1 | 2/2008 | Ellis-Behnke et al. |
| 2008/0091233 A1 | 4/2008 | Ellis-Behnke et al. |
| 2008/0274979 A1 | 11/2008 | Ellis-Behnke et al. |
| 2009/0111734 A1 | 4/2009 | Ellis-Behnke et al. |
| 2009/0162437 A1 | 6/2009 | Horii et al. |
| 2010/0311640 A1 | 12/2010 | Genove et al. |
| 2012/0010140 A1 | 1/2012 | Ellis-Behnke et al. |
| 2012/0085262 A1 | 4/2012 | Klimov et al. |
| 2015/0328279 A1 | 11/2015 | Ellis-Behnke et al. |

FOREIGN PATENT DOCUMENTS

| | | |
|---|---|---|
| WO | WO-98/58967 A1 | 12/1998 |
| WO | WO-99/52574 A1 | 10/1999 |
| WO | WO 02/058749 A2 | 8/2002 |
| WO | WO-02/062969 A2 | 8/2002 |
| WO | WO-03/006043 A1 | 1/2003 |
| WO | WO-03/084980 A2 | 10/2003 |
| WO | WO-03/096972 A2 | 11/2003 |
| WO | WO-2004/007532 A2 | 1/2004 |
| WO | WO 2005/014615 * | 2/2005 |
| WO | WO-2006/014570 A2 | 2/2006 |
| WO | WO 2006/036826 A2 | 4/2006 |
| WO | WO-2006/076042 A2 | 7/2006 |
| WO | WO-2006/116524 A1 | 11/2006 |
| WO | WO 2006/116524 A1 | 11/2006 |
| WO | WO-2007/142757 A2 | 12/2007 |
| WO | WO 2008/113030 A2 | 9/2008 |
| WO | WO-2008/134544 A1 | 11/2008 |
| WO | WO 2013/126776 A1 | 8/2013 |

OTHER PUBLICATIONS

Armstrong et al ('Blood flows within and among rat muscles as a function of time during high speed treadmill exercise' J Physiol 1983 v344 pp. 189-208).*
Water structure and science (retrieved from http://www.lsbu.ac.uk/water/molecule.html on Dec. 21, 2011 5 pages).*
Kinsey et al ('Molecules in motion:influences of diffusion on metabolic structure and function in skeletal muscle' The Journal of Experimental Biology 2011 v214 pp. 263-274).*
Davis et al., "Injectable Self-Assembling Peptide Nanofibers Create Intramyocardial Microenvironments for Endothelial Cells", Circulation, vol. III, Feb. 2005, pp. 442-450.
Ellis-Behnke et al., "Crystal Clear Surgery with Self-Assembling Molecules that Act as a Bio Barrier in the Brain and Intestine", Nanomedicine: Nanotechnology Biology and Medicine, vol. 1, Sep. 2005; pp. 269-270.
Narmoneva et al., "Self-Assembling Short Oligopeptides and the Promotion of Angiogenesis", Biomaterials, vol. 26, Aug. 2005 pp. 4837-4846.
Bokhari et al., "The Enhancement of Osteoblast Growth and Differentiation in Vitro on a Peptide Hydrogel-PolyHIPE Polymer Hybrid Material", Biomaterials, vol. 26, Sep. 2005, pp. 5198-5208.
Ellis-Behnke et al., "Nano Neuro Knitting: Peptide Nanofiber Scaffold for Brain Repair and Axon Regeneration with Functional Return of Vision", Proceedings of the National Academy of Sciences, USA, vol. 103, Mar. 2005, pp. 5054-5059.
Zhang et al., "Designer Self-Assembling Peptide Nanofiber Scaffolds for 3D Tissue Cell Cultures", Seminars in Cancer Biology, vol. 15, Oct. 2005, pp. 413-420.
Genové et al., "The Effect of Functionalized Self-Assembling Peptide Scaffolds on Human Aortic Endothelial Cell Function", Biomaterials, vol. 26, Jun. 2005 pp. 3341-3351.
Ball, P., "Brain Knitting," naterials@nature.com Apr. 13, 2006.
Bullis, K., "Nanohealing," Nanotechnology.
Caplan et al., "Control of self-assembling oligopeptide matrix formation through systematic variation of amino acid sequence," Biomaterials 2002, 23, 219-227.
Caplan et al., "Self-assembly of a beta-sheet protein governed by relief of electrostatic repulsion relative to van der Waals attraction," Biomacromolecules 2000, 1, 627-631.
Crowston, J. et al., "New Optic Nerve?" International Claucoma Review, The Journal for the Association of International Glaucoma Societies, (Meeting) Reports (IGR 9-1 Jun. 2007.
Ellis-Behnke et al., "Molecular repair of the brain using self-assembling peptides," Chim. Oggi. 2006, 24(4), 42-45.
Ellis-Behnke et al, "Molecular Restoration of the Body: Nano Neuro Knitting for Brain Repair," JEAAM & BAAMJ, Issue 4.
Ellis-Behnke et al., "Nano hemostat solution: immediate hemostasis at the nanoscale," Nanomedicine: Nanotechnology, Biology and Medicine 2006, 2(4), 207-215.
Ellis-Behnke, R., "Nano Neuro Knitting: Peptide Nanofiber Scaffold for Brain Repair and Axon Regeneration with Functional Return of Vision," Nature Reviews/Neuroscience, Research Highlights, vol. 7, May 2006, p. 1.
Ellis-Behnke et al., Using Nanotechnology to Design Potential Therapies for CNS Regeneration. Curr Phar Design 2007, 13(24): 2519-2528.
Hampton, T., "Healing Power Found in Nano Knitting," JAMA, Jan. 3, 2007, vol. 297, No. 1 p. 31.
Hartgerink, J., "New Material Stops Bleeding in a Hurry," Nature Nanotechnology, vol. 1, Dec. 2006, p. 166-167.
Holmes et al., "Extensive neurite outgrowth and active synapse formation on self-assembling peptide scaffolds," PNAS 2000, 97(12), 6728-6733.
Guo et al., "Reknitting the Injured Spinal Cord by Self-Assembling Peptide Nanofiber Scaffold," Nanomedicine: Nanotechnology, Biology, and Medicine, 3 (2007) 311-321.
Leon et al., "Mechanical properties of a self-assembling oligopeptide matrix," J. Biomater. Sci. Polymer Edn. 1998, 9(3), 297-312.
Schneider et al., "Behavioral testing and preliminary analysis of the hamster visual system," Nat. Prot. 2006, 1(4), 1898-1905.
Trafton, A., "MIT TechTalk," vol. 51—No. 5 Oct. 18, 2006, "New Material Halts Bleeding," p. 1-2.
Teather et al., "Differential induction of c-JUN and Fos-like proteins in rat hippocampus and dorsal striatum after training in two water maze tasks," Neurobiol Learn. Mem. 2005, 84(2), 75-84.
Thomas, L., "Nano Neuro Knitting Repairs Injured Brain," The Lancet Neurology, vol. 5, Issue 5, May 2006, p. 386.
Tu et al., "Bottom-up design of biomimetic assemblies," Advanced Drug Delivery Reviews 2004, 56, 1537-1563.
International Search Report dated Sep. 28, 2006 in PCT/US2006/015850.
Written Opinion dated Sep. 28, 2006 in PCT/US2006/015850.
http://web.mit.edu/newsoffice/2006/hemostasis Oct. 10, 2006.
http://newsvote.bbc.co.uk/mpapps/pagetools/print/news.bbc.co.uk/1/hi/health/5413592.stm Oct. 15, 2006.
http://www.allheadlinenews.com/articles/7005131407 Oct. 10, 2006.
http://abc.net.au/cgi-bin/common/printfriendly.pl?/science/news/stories/2006/1759654.htm Oct. 10, 2006.
http://www.rsc.org/chemistryworld/News/2006/October/10080601.asp Oct. 10, 2006.
http://www.thestandard.com.hk/news_detail.asp?pp_cat=11&art_id+29141&sid=10313489&con . . . Oct. 10, 2006.
http://www.dailyindia.com/show/68390.php/Study:-Biodegradable-liquids-halt-bleeding Oct. 10, 2006.
http://64.233.179.104/translate_c?hl=en&u=htp://www.dradio.de/dlf/sendungen/forschak/55243 . . . Oct. 10, 2006.
http://www.foxnews.com/printer_friendly_story/0,3566,219241,00.html Oct. 10, 2006.
http://www.whatsnextnetwork.com/technology/index/php/2006/10/10/biodegradable_liquids_can . . . Oct. 15, 2006.
http://license.icopyright.net/user/viewFreeUse.act?fuid=MTc0OTA4 Oct. 10, 2006.

(56) References Cited

OTHER PUBLICATIONS http://www.thestar.com/NASApp/cs/ContentServer?pagename=thestar/Layout/Article_PrintFrie . . . Oct. 15, 2006.
http://www.technologyreview.com/printer_friendly_article.aspx?id=17597 Oct. 10, 2006.
http://www.sciam.com/article.cmf?chanID=sa003&articleID=000D056A-AAFC-1526-AAB683 . . . Oct. 10, 2006.
http://sciencenow.sciencemag.org/cgi/content/full/2006/1010/3 Oct. 10, 2006.
http://www.scenta.co.uk/scenta/news.cfm?FaAreal1=widgets.content_print_1&cit_id=1183846 Oct. 10, 2006.
http://www.sacbee.com/101/v-print/story/36341.html Oct. 10, 2006.
http://www.alertnet.org/printable htm?URL=/thenews/newsdesk/N09252559.htm Oct. 10, 2006.
http://www.newscientisttech.com/article.ns?id=dn10265&print=true Oct. 12, 2006.
http://www.newindpress.com/Print.asp?ID=IE320061011052721 Oct. 11, 2006.
http://www.nanochina.cn/english/index.php?option=content&task=view&id=681&Itemid=1 Nov. 11, 2006.
http://www.mumbaimirror.com/nmirror/mmprint.asp?frmprn=yes&sectid=16&articleid=101620 Oct. 17, 2006.
http://popsci.com/popsci/medicine/c8Oec6f39986c010vgnvcm1000004eecbccdrcrd/5.html Aug. 11, 2006.
http://www.iran-daily.com/1385/2545/html/science.htm Aug. 11, 2006.
http://www.dddmag.com/ShowPR.aspx?PUBCODE=016&ACCT=1600000100&ISSUE=0609& . . . Sep. 22, 2006.
http://www.stemcellschina.com/content/view/163/88/ Aug. 11, 2006.
http://discovermagazme.com/2006/oct/liquid-stop-bleeding/article_print Dec. 22, 2007.
http://discovermagazine.com/2007/feb/nanoliquid-bleeding-protein-clot/article_print Dec. 22, 2007.
ACS Chemical Biology, 1(3), 116-122, 10.1021/cb600147p Apr. 21, 2006, "Clsoing the CNS Gap".
International Search Report and Written Opinion for International Patent Application Serial No. PCT/US2007/010041, mailed Aug. 7, 2008.
International Search Report and Written Opinion for International Patent Application Serial No. PCT/US2008/057104, mailed Feb. 9, 2009.
[No Author Listed] "Conform." Merriam Webster Dictionary. Available at http://www.merriam-webster.com/dictionary/conform. Last accessed Aug. 4, 2009. 2 pages.
[No Author Listed] "Designing Custom Peptides." SIGMA Genosys. Dec. 16, 2004. Available at http://www.sigma-genosys.com/peptide_design.asp. Last accessed Dec. 16, 2004. 1-2. 2 pages.
[No Author Listed] "Endometriosis." Merck Manual Professional. Available at www.merck.com. Last accessed Aug. 4, 2009. 5 pages.
[No Author Listed] "FDA Approves Sealant to Prevent Cerebrospinal Fluid Leaks After Brain Surgery." FDA U.S. Food and Drug Adminstration. Press Release. Apr. 7, 2005. Available at http://www.fda.gov/NewsEvents/Newsroom/PressAnnouncements/2005/ucm108428.htm. Last accessed Jan. 28, 2011. 1 page.
[No Author Listed] "Intestinal Obstruction." Merck Manual Professional. Available at www.merck.com. Last accessed Aug. 4, 2009. 4 pages.
[No Author Listed] "Keloid and Hypertrophic Scar: Treatment & Medication." Available at http://emedicine.medscape.com/article/1057599-treatmemt. Last accessed Aug. 4, 2009. 16 pages.
[No Author Listed] "Keloids." Merck Manual Professional. Avaialbel at www.merck.com. Last accessed Aug. 4, 2009. 1 page.
[No Author Listed] "Residue." Dictionary definition. Avaialble at from http://dictionary.reference.com/browse/residue. Last accessed Jul. 13, 2009. 4 pages.
[No Author Listed] "Tubal Dysfunction and Pelvice Lesions." Merck Manual Professional. Available at www.merck.com. Last accessed Aug. 4, 2009. 2 pages.
Aggeli et al., Self-assembling peptide polyelectrolyte beta-sheet complexes form nematic hydrogels. Angew Chem Int Ed Engl. Nov. 24, 2003;42(45):5603-6.
Allen et al., Variation of the axial haem ligands and haem-binding motif as a probe of the *Escherichia coli* c-type cytochrome maturation (Ccm) system. Biochem J. Nov. 1, 2003;375(Pt 3):721-8.
Benita et al., Characterization of drug-loaded poly(d,l-lactide) microspheres. J. Pharm. Sci. 1984;73(12): 1721-1724.
Berendsen, A Glimpse of the Holy Grail? Science. 1998;282:642-643.
Bradley et al., Limits of cooperativity in a structurally modular protein: Response of the Notch Ankyrin Domain to analogous alanine substitutions in each repeat. J. Mol. Biol. 2002;324:373-386.
Frechet, Dendrimers and supramolecular chemistry. Proc. Natl. Acad. Sci. USA. 2002;99(8):4782-4787.
Gruen et al., Interaction of amino acids with silver(I) ions. Biochim Biophys Acta. Mar. 28, 1975;386(1):270-4.
Hill et al., A field guide to foldamers. Chem. Rev. 2001;101(12):3983-4012.
Hwang et al., Self-assembling biomaterials: liquid crystal phases of cholesteryl oligo(L-lactic acid) and their interactions with cells. Proc Natl Acad Sci U S A. Jul. 23, 2002;99(15):9662-7. Epub Jul. 15, 2002.
Kendhale et al., Isotactic N-alkyl acrylamide oligomers assume self-assembled sheet structure: first unequivocal evidence from crystal structure. Chem. Comm. (Camb). 2006;26:2756-2758.
Ma et al., Supramolecular polymer chemistry: self-assembling dendrimers using the DDA.AAD (GC-like) hydrogen bonding motif. J. Am. Chem. Soc. 2002;124(46):13757-13769.
Mathiowitz et al., Morphology of polyanhydride microsphere delivery system. Scanning Microscopy. 1990;4(2):329-340.
Mathiowitz et al., Novel microcapsules for delivery systems. Reactive Polymers. 1987;6:275-283.
Mathiowitz et al., Polyanhydride microspheres as drug carriers I. Hot-melt microencapsulation. J. Controlled Release. 1987;5(1)13-22.
Mathiowitz et al., Polyanhydride microspheres as drug carriers II. microencapsulation by solvent removal. J. Appl. Polymer Sci. 1988;35:755-774.
Mathiowitz et al., Polyanhydride microspheres. IV: Morphology and characterization of systems made by spray drying. J. Appl. Polymer Sci. 1992;45:125-134.
Ngo et al., Computational Complexity, Protein Structure Prediction, and the Levinthal Paradox. In: The Protein Folding Problem and Tertiary Structure Prediction. K. Merc Jr. et al., eds. 1994:491-495.
Rudinger, Characteristics of the amino acids as components of a peptide hormone sequence. In: Peptide Hormones, Parsons, ed. University Park Press, Jun. 1976: 1-7.
Sawhney et al., Bioerodible hydrogels based on photopolymerized poly(ethylene glycol)-co-poly(ahydroxy acid) diacrylate macromers. Macromolecules. 1993;26(4):581-587.
Schinzel et al., The phosphate recognition site of *Escherichia coli* maltodextrin phosphorylase. FEBS. Jul. 1991;286(1,2)125-128.
Sheihet et al., Hydrophobic drug delivery by self-assembling triblock copolymer-derived nanospheres. Biomacromolecules. Sep.-Oct. 2005;6(5):2726-31.
Voet et al., 3. Abnormal Hemoglobins. In: Biochemistry. Second Ed., John Wiley & Sons, Inc. 1995:235-241.
Zhang et al., Peptide self-assembly in functional polymer science and engineering. Reactive & Functional Polymers. 1999;41:91-102.
Zhang et al., Self-assembling peptides in biology, materials science and engineering. Peptide Science—Present and Future. 1999;1997:737-44.
Zhang et al., Self-complementary oligopeptide matrices support mammalian cell attachment. Biomaterials. 1995;16(18):1385-1393.
Zhang et al., Spontaneous assembly of self-complementary oligopeptide to form a stable macroscopic membrane. Proc. Natl. Acad. Sci. USA. 1993;90(8):3334-3338.
Zimmerman et al., Self-assembing dendrimers. Science. 1996;271(5252):1095-1098.

(56) References Cited

OTHER PUBLICATIONS

[No Author Listed], Patent Assignment Abstract of Title for U.S. Appl. No. 60/674,612, filed Apr. 25, 2005. 2 pgs.
[No Author Listed], Patent Assignment Abstract of Title for U.S. Appl. No. 60/758,827, filed Jan. 13, 2006. 2 pgs.
Zhang et al., Building from the bottom up. Materials today. Review Feature.May 2003;20-27.
Zhang et al., Emerging biological materials through molecular self-assembly. Biotechnology Advances. 2002:20;321-339.
[No Author Listed] Analytical Data Sheet B05246. Product No. 4056169. Product H-Arg-Ala-Asp-Ala-Arg-Ala-Asp-Ala-Arg-Ala-Asp-Ala-Arg-Ala-Asp-Ala-$NH_2$. Molecular formula $C_{64}H_{111}N_{29}O_{24}$. Last updated Jul. 9, 2007. 3 pages.
[No Author Listed] Analytical Data Sheet B05779. Product No. 4056167. Product Ac-Arg-Ala-Asp-Ala-Arg-Ala-Asp-Ala-Arg-Ala-Asp-Ala-Arg-Ala-Asp-Ala-$NH_2$. Molecular formula $C_{66}H_{113}N_{29}O_{25}$. Last updated Sep. 17, 2008. 3 pages.
[No Author Listed] BD BioSciences. Invoice. Dec. 21, 2006.1 page.
[No Author Listed], Amino Acid Analysis Report. Protein Structure Core Facility. Univ. of Nebraska Medical Center. Feb. 8, 2007.1-5.
[No Author Listed], BD™ PuraMatrix™ Peptide Hydrogel. Catalog No. 354250: Guidelines for Use. 2004. 1-16.
Chen et al., A hybrid silk/RADA-based fibrous scaffold with triple hierarchy for ligament regeneration. Tissue Engineering. 2012; 18(13-14):1399-1409.
Declaration of Steven A. Kates, Ph.D. for Japanese Patent Application No. 2008-509090 signed Dec. 12, 2012.1-6.
Declaration of Steven A. Kates, Ph.D. for Korean Patent Application No. 10-2010-7019627 signed Jul. 3, 2014.1-4.
Exhibit A to Declaration of Steven A. Kates, Ph.D. for Korean Patent Application No. 10-2010-7019627 signed Jul. 3, 2014.1-4. Curriculum Vitae of Steven A. Kates, Ph.D. Dated Feb. 2014. 7 pages.
Exhibit B to Declaration of Steven A. Kates, Ph.D for Korean Patent Application No. 10-2010-7019627 signed Jul. 3, 2014.1-4. Listing of Publications by Steven Kates dated Feb. 2014. 14 pages.
Exhibit C to Declaration of Steven A. Kates, Ph.D. For Korean Patent Application No. 10-2010-7019627 signed Jul. 3, 2014.1-4.BD PuraMatrix Peptide Hydrogel Sample Information. Date acquired May 7, 2014. 2 pages.
Exhibit D to Declaration of Steven A. Kates, Ph.D. for Korean Patent Application No. 10-2010-7019627 signed Jul. 3, 2014.1-4. PuraMatric Mass Spectromly result dated May 7, 2014. 1 page.
Mishra et al., Ultrasmall natural peptides self-assemble to strong temperature-resistant helical fibers in scaffolds suitable for tissue engineering. Nano Today. 2011; 6(3):232-239.
Semino et al., Functional differentiation of hepatocyte-like spheroid structures from putative liver progenitor cells in three-dimensional peptide scaffolds. Differentiation. Jun. 2003;71(4-5):262-70.
Notice of Opposition to a European Patent dated Jan. 20, 2014 for Application No. EP06751519.7.
Notice of Opposition to a European Patent dated Mar. 12, 2014 for Application No. EP06751519.7.
Email Correspondence regarding U.S. Appl. Nos. 12/049,190 and 11/411,745. [Mar. 27, 2015; 3:36pm].
Email Correspondence regarding U.S. Appl. Nos. 12/049,190 and 11/411,745. [Mar. 29, 2015; 8:44pm].
Email Correspondence regarding U.S. Appl. Nos. 12/049,190 and 11/411,745. [Mar. 30, 2015; 6:20am].
Email Correspondence regarding U.S. Appl. No. 11/411,745. [Mar. 30, 2015; 10:48am].
Email Correspondence regarding U.S. Appl. Nos. 12/049,190 and 11/411,745. [Mar. 30, 2015; 11:50am].
Email Correspondence regarding U.S. Appl. Nos. 12/049,190 and 11/411,745. [Mar. 30, 2015; 3:57pm].
Email Correspondence regarding U.S. Appl. Nos. 12/049,190 and 11/411,745. [Mar. 30, 2015; 3:59pm].
Email Correspondence regarding U.S. Appl. No. 11/411,745. [Mar. 30, 2015; 5:12pm].
Email Correspondence regarding U.S. Appl. Nos. 12/049,190 and 11/411,745. [Mar. 30, 2015; 5:13pm].
Email Correspondence regarding U.S. Appl. Nos. 12/049,190 and 11/411,745. [Mar. 30, 2015; 5:20pm].
Email Correspondence regarding U.S. Appl. No. 11/411,745. [Mar. 30, 2015; 5:41pm].
Email Correspondence regarding U.S. Appl. No. 11/411,745. [Mar. 30, 2015; 5:49pm].
Email Correspondence regarding U.S. Appl. No. 11/411,745. [Mar. 30, 2015; 5:54pm].
Email Correspondence regarding U.S. Appl. No. 11/411,745. [Mar. 30, 2015; 6:20pm].
Email Correspondence regarding U.S. Appl. No. 11/411,745. [Mar. 30, 2015; 6:28pm].
Email Correspondence regarding U.S. Appl. No. 11/411,745. [Mar. 30, 2015; 7:00pm].
Email Correspondence regarding U.S. Appl. No. 11/411,745. [Mar. 30, 2015; 8:19pm].
Email Correspondence regarding U.S. Appl. No. 11/411,745. [Mar. 30, 2015; 9:16pm].
Email Correspondence regarding U.S. Appl. No. 11/411,745. [Mar. 31, 2015; 9:22am].
Email Correspondence regarding U.S. Appl. No. 11/411,745. [Mar. 31, 2015; 10:01am].
Email Correspondence regarding U.S. Appl. No. 11/411,745. [Mar. 31, 2015; 11:04am].
Email Correspondence regarding U.S. Appl. No. 11/411,745. [Mar. 31, 2015; 11:19am].
Email Correspondence regarding U.S. Appl. No. 11/411,745. [Mar. 31, 2015; 11:21am].
Email Correspondence regarding U.S. Appl. No. 11/411,745. [Mar. 31, 2015; 11:23am].
Email Correspondence regarding U.S. Appl. No. 11/411,745. [Mar. 31, 2015; 12:15pm].
Email Correspondence regarding U.S. Appl. No. 11/411,745. [Mar. 31, 2015; 12:20pm].
Email Correspondence regarding U.S. Appl. No. 11/411,745. [Mar. 31, 2015; 12:22pm].
Email Correspondence regarding U.S. Appl. No. 11/411,745. [Mar. 31, 2015; 12:42pm].
Email Correspondence regarding U.S. Appl. No. 11/411,745. [Mar. 31, 2015; 2:58pm].
Email Correspondence regarding U.S. Appl. No. 11/411,745. [Mar. 31, 2015; 3:15pm].
Email Correspondence regarding U.S. Appl. No. 11/411,745. [Mar. 31, 2015; 3:57pm].
Email Correspondence regarding U.S. Appl. No. 11/411,745. [Mar. 31, 2015; 4:14pm].
Email Correspondence regarding shared videos (see below) for USPTO: Mar. 31, 2015; 4:54pm.
Ellis-Behnke, MIT, Arch Thrapeutics, Inc., Crystal Clear Surgery (TM): Removal of Dura. 2013. Referred to in Email Correspondence: Mar. 31, 2015; 4:54pm. (.mov file; DVD enclosed).
Arch Therapeutics, Inc., Femoral A/V Transection. 2013. Referred to in Email Correspondence: Mar. 31, 2015; 4:54pm. (.mov file; DVD enclosed).
Ellis-Behnke, Infusion in femoral vein; bolus train of 3%. Referred to in Email Correspondence: Mar. 31, 2015; 4:54pm. (.mp4 file; DVD enclosed).
Email Correspondence regarding U.S. Appl. No. 11/411,745. [Apr. 1, 2015; 11:01am].
Email Correspondence (and attachment included therein) regarding U.S. Appl. No. 11/411,745. [Apr. 1, 2015; 11:24am].
Email Correspondence regarding U.S. Appl. No. 11/411,745. [Apr. 1, 2015; 2:20pm].
Email Correspondence regarding U.S. Appl. No. 11/411,745. [Apr. 1, 2015; 2:27pm].
Email Correspondence regarding U.S. Appl. No. 11/411,745. [Apr. 1, 2015; 4:14pm].
Email Correspondence regarding U.S. Appl. No. 11/411,745. [Apr. 1, 2015; 4:19pm].
Email Correspondence regarding U.S. Appl. No. 11/411,745. [Apr. 3, 2015; 2:39pm].
Email Correspondence regarding U.S. Appl. No. 11/411,745. [Apr. 3, 2015; 2:55pm].

(56) References Cited

OTHER PUBLICATIONS

Email Correspondence regarding U.S. Appl. No. 11/411,745. [Apr. 3, 2015; 2:57pm].
Email Correspondence regarding U.S. Appl. No. 11/411,745. [Apr. 3, 2015; 2:58pm].
Email Correspondence regarding U.S. Appl. No. 11/411,745. [Apr. 3, 2015; 3:37pm].
Email Correspondence regarding U.S. Appl. No. 11/411,745. [Apr. 3, 2015; 3:42pm].
Email Correspondence regarding U.S. Appl. No. 11/411,745. [Apr. 3, 2015; 3:44pm].
Email Correspondence regarding U.S. Appl. No. 11/411,745. [Apr. 3, 2015; 3:47pm].
Extended European Search Report for EP 10181924.1 mailed May 11, 2011.
Altman et al., Conformational behavior of ionic self-complementary peptides. Protein Sci. Jun. 2000;9(6):1095-105.
Chen, Self-assembly of ionic-complementary peptides: a physiochemical viewpoint. Colloids Surf A Physicochem Eng Asp. 2005;261:3-24.
Semino et al., Entrapment of migrating hippocampal neural cells in three-dimensional peptide nanofiber scaffold. Tissue Eng. Mar.-Apr. 2004;10(3-4):643-55.
Shen et al., Artificial extracellular matrices can be used for in vitro control of stem cell differentiation. 2003 Summer Bioengineering Conference. Sonesta Beach Resort. Key Biscayne, Florida. Jun. 25-29, 2003:1 page. Available at http://www.tulane.edu/{sbc2003/pdfdocs/0357.PDF. Retrieved on Apr. 27, 2011.
Yokoi et al., Dynamic reassembly of peptide RADA16 nanofiber scaffold. Proc Natl Acad Sci U S A. Jun. 14, 2005;102(24):8414-9. Epub Jun. 6, 2005.
Zhang, Designing novel materials and molecular machines. Economic Perspectives. 2005:22-24. Available at http://www.esm.psu.edu/{ax14/lakhtakia/Documents/ijee1005.pdf. Retrieved on Apr. 28, 2011.
[No Author Listed] Product List. PuraMatrix™. Apr. 16, 2005. 2 pages, http://web.archive.org/web/20050416043834/http://www.3d-matrix.co.jp/pr02.html.
[No Author Listed] FAQs, Apr. 15, 2005, Available at http://web.archive.org/web/20050415003206/http://www.3d-matrix.co.jp/fq01.html. Last accessed Sep. 13, 2011, 4 pages.
[No Author Listed] Product Features. Apr. 16, 2005. Available at http://web.archive.org/web/20050416044014/http://www.3d-matrix.co.jp/pr03.html. Last accessed Sep. 13, 2011. 1 page.
[No Author Listed] Announcement of PuraMatrix™, Apr. 15, 2005. Available at http://web.archive.org/web/20050415004502/http://www.3d-matrix.co.jp/pr01.html. Last accessed Sep. 13, 2011. 2 pages.
[No Author Listed] Details of characteristics of PuraMatrix™, Apr. 16, 2005. Available at http://web.archive.org/web/2005041604410/http://www.3d-matrix.co.jp/dl_file/Competition_Comparison.pdf. Last accessed Sep. 13, 2011, 4 pages.
Atala, Tissue engineering and regenerative medicine: concepts for clinical application. Rejuvenation Res. 2004 Spring:7(1):15-31.
Eisenbud et al., Hydrogel Wound Dressings: Where do we stand in 2003? Ostomy Wound Manage (OWM): Original Research. Oct. 2003, 49(10):52-7.
Ellis-Behnke. At the nanoscale: nanohemostat, a new class of hemostatic agent. Wiley Interdiscip Rev Nanomed Nanobiotechnol. Jan.-Feb. 2011:3(1):70-8.
Gervaso et al., The biomaterialist's task: scaffold biomaterials and fabrication technologies, Joints, 2013. 1(3): 130-7.
Hilton et al., Wound dressings in diabetic foot disease, Clin Infect Dis. Aug. 1, 2004;39 Suppl 2:5100-3.
Kauvar et al., The epidemiology and modern management of traumatic hemorrhage: US and international perspectives. Review. Suppl S. Critical Care. 2005. 9: S1-S9.
Komatsu et al., The neutral Self Assembling Peptide Hydrogel SPG-178 as a Topical Hemostatic Agent. PLOS ONE. Jul. 2014. 9(7):e102778. DOI: 10.1371/journal.pone.0102778.
Osterman et al., Design and Characterization of Peptides with Amphiphiliac β-Strand Structures. Journal of Cellular Biochemistry, 1985. 29:57-72.
Song et al., Hemostatic Efficacy of Biological Self-Assembling Peptide Nanofibers in a Rat Kidney. Model. Macromol Biosci. 2010. 10:33-9. DOI: 10.1002/mabi.200900129.
Takei, 3-Dimensional Cell Culture Scaffold for Everyone Drug Screening, Tissue Engineering and Cancer Biology.AATEX. 2006. 11(3): 170-176.
Tortora et al., "Skin Wound Healing." Principles of Human Anatomy 5th ed. 1989. 98-100.
Ye et al., Temperature and pH effects on biophysical and morphological properties of self-assembling peptide RADA16-1‡. J Peptide Sci. Jan. 14, 2008, 14:152-62. DOI: 10.1002/psc.988.
U.S. Appl. No. 12/199,670, filed Aug. 27, 2008, Ellis-Behnke et al.
U.S. Appl. No. 11/796,132, filed Apr. 25, 2007, Ellis-Behnke et al.
EP 10181924.1, May 11, 2011, Extended European Search Report.

\* cited by examiner (SEQ. ID. NO: 1)

SEQUENCE LISTING

```
<160> NUMBER OF SEQ ID NOS: 76

<210> SEQ ID NO 1
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 1

Arg Ala Asp Ala Arg Ala Asp Ala Arg Ala Asp Ala Arg Ala Asp Ala
 1               5                  10                  15
```

-continued

```
<210> SEQ ID NO 2
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 2

Arg Ala Asp Arg Asp Ala Arg Ala Asp Arg Asp Ala
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 3

Arg Ala Asp Ala Arg Ala Asp Ala
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 5

Arg Ala Arg Ala Asp Ala Asp Ala
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 7

Ala Glu Ala Lys Ala Glu Ala Lys
1               5
```

-continued

```
<210> SEQ ID NO 8
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 11

Lys Ala Asp Ala Lys Ala Asp Ala
1               5

<210> SEQ ID NO 12
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 12

Ala Glu Ala Glu Ala His Ala His Ala Glu Ala Glu Ala His Ala His
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 13

Ala Glu Ala Glu Ala His Ala His
1               5
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 15

Phe Glu Phe Lys Phe Glu Phe Lys
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 19

Ala Glu Ala Glu Ala Glu Ala Glu Ala Lys Ala Lys
1               5                   10
```

```
<210> SEQ ID NO 20
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 20

Ala Glu Ala Glu Ala Lys Ala Lys
1               5

<210> SEQ ID NO 21
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 21

Lys Ala Lys Ala Lys Ala Lys Ala Glu Ala Glu Ala Glu Ala Glu Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 22

Ala Glu Ala Glu Ala Glu Ala Glu Ala Lys Ala Lys Ala Lys Ala Lys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 23

Arg Ala Arg Ala Arg Ala Arg Ala Asp Ala Asp Ala Asp Ala Asp Ala
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 24

Ala Asp Ala Asp Ala Asp Ala Asp Ala Arg Ala Arg Ala Arg Ala Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 25

Asp Ala Asp Ala Asp Ala Asp Ala Arg Ala Arg Ala Arg Ala Arg Ala
1               5                   10                  15
```

```
<210> SEQ ID NO 26
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 26

Ala Asp Ala Asp Ala Asp Ala Asp Ala Arg Ala Arg Ala Arg Ala Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 27

His Glu His Glu His Lys His Lys His Glu His Glu His Lys His Lys
1               5                   10                  15

<210> SEQ ID NO 28
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 28

His Glu His Glu His Lys His Lys
1               5

<210> SEQ ID NO 29
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 29

Val Glu Val Glu Val Glu Val Glu Val Glu Val Glu Val Glu Val Glu
1               5                   10                  15

Val Glu Val Glu
            20

<210> SEQ ID NO 30
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 30

Arg Phe Arg Phe Arg Phe Arg Phe Arg Phe Arg Phe Arg Phe Arg Phe
1               5                   10                  15

Arg Phe Arg Phe
            20

<210> SEQ ID NO 31
<211> LENGTH: 12
<212> TYPE: PRT
<213> ORGANISM: Artificial Sequence
<220> FEATURE:
<223> OTHER INFORMATION: Synthetically generated peptide
```

```
<400> SEQUENCE: 31

Arg Ala Asp Ala Arg Ala Asp Ala Arg Ala Asp Ala
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 32

Ala Lys Ala Lys Ala Glu Ala Glu Ala Lys Ala Lys Ala Glu Ala Glu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 33

Ala Lys Ala Glu Ala Lys Ala Glu Ala Lys Ala Glu Ala Lys Ala Glu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 34

Glu Ala Lys Ala Glu Ala Lys Ala Glu Ala Lys Ala Glu Ala Lys Ala
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 35

Lys Ala Glu Ala Lys Ala Glu Ala Lys Ala Glu Ala Lys Ala Glu Ala
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 36

Ala Asp Ala Asp Ala Arg Ala Arg Ala Asp Ala Asp Ala Arg Ala Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetically generated peptide
```

<400> SEQUENCE: 37

Ala Arg Ala Asp Ala Arg Ala Asp Ala Arg Ala Asp Ala Arg Ala Asp
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 38

Asp Ala Arg Ala Asp Ala Arg Ala Asp Ala Arg Ala Asp Ala Arg Ala
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 39

Ala Asp Ala Arg Ala Asp Ala Arg Ala Asp Ala Arg Ala Asp Ala Arg
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 40

Ala Arg Ala Asp Ala Lys Ala Glu Ala Arg Ala Asp Ala Lys Ala Glu
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 41

Ala Lys Ala Glu Ala Arg Ala Asp Ala Lys Ala Glu Ala Arg Ala Asp
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 42

Ala Arg Ala Lys Ala Asp Ala Glu Ala Arg Ala Lys Ala Asp Ala Glu
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetically generated peptide

```
<400> SEQUENCE: 43

Ala Lys Ala Arg Ala Glu Ala Asp Ala Lys Ala Arg Ala Asp Ala Glu
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 44

Ala Gln Ala Gln Ala Gln Ala Gln Ala Gln Ala Gln Ala Gln Ala Gln
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 45

Val Gln Val Gln Val Gln Val Gln Val Gln Val Gln Val Gln Val Gln
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 46

Tyr Gln Tyr Gln Tyr Gln Tyr Gln Tyr Gln Tyr Gln Tyr Gln Tyr Gln
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 47

His Gln His Gln His Gln His Gln His Gln His Gln His Gln His Gln
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 48

Ala Asn Ala Asn Ala Asn Ala Asn Ala Asn Ala Asn Ala Asn Ala
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetically generated peptide
```

```
<400> SEQUENCE: 49

Val Asn Val Asn Val Asn Val Asn Val Asn Val Asn Val Asn Val
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 50

Tyr Asn Tyr Asn Tyr Asn Tyr Asn Tyr Asn Tyr Asn Tyr Asn Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 51

His Asn His Asn His Asn His Asn His Asn His Asn His Asn His
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 52

Ala Asn Ala Gln Ala Asn Ala Gln Ala Asn Ala Gln Ala Asn Ala Gln
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 53

Ala Gln Ala Asn Ala Gln Ala Asn Ala Gln Ala Asn Ala Gln Ala
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 54

Val Asn Val Gln Val Asn Val Gln Val Asn Val Gln Val Asn Val Gln
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetically generated peptide
```

```
<400> SEQUENCE: 55

Val Gln Val Asn Val Gln Val Asn Val Gln Val Asn Val Gln Val
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 56

Tyr Asn Tyr Gln Tyr Asn Tyr Gln Tyr Asn Tyr Gln Tyr Asn Tyr Gln
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 57

Tyr Gln Tyr Asn Tyr Gln Tyr Asn Tyr Gln Tyr Asn Tyr Gln Tyr
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 58

His Asn His Gln His Asn His Gln His Asn His Gln His Asn His Gln
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 59

His Gln His Asn His Gln His Asn His Gln His Asn His Gln His
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 60

Ala Lys Ala Gln Ala Asp Ala Lys Ala Gln Ala Asp Ala Lys Ala Gln
1               5                   10                  15

Ala Asp

<210> SEQ ID NO 61
<211> LENGTH: 18
<212> TYPE: PRT
<213> ORGANISM: Artificial Sequence
<220> FEATURE:
<223> OTHER INFORMATION: Synthetically generated peptide
```

-continued

```
<400> SEQUENCE: 61

Val Lys Val Gln Val Asp Val Lys Val Gln Val Asp Val Lys Val Gln
1               5                   10                  15

Val Asp

<210> SEQ ID NO 62
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 62

Tyr Lys Tyr Gln Tyr Asp Tyr Lys Tyr Gln Tyr Asp Tyr Lys Tyr Gln
1               5                   10                  15

Tyr Asp

<210> SEQ ID NO 63
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 63

His Lys His Gln His Asp His Lys His Gln His Asp His Lys His Gln
1               5                   10                  15

His Asp

<210> SEQ ID NO 64
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 64

Ala Asp Ala Asp Ala Lys Ala Lys Ala Asp Ala Asp Ala Lys Ala Lys
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 65

Lys Ala Lys Ala Lys Ala Lys Ala Lys Ala Lys Ala Lys Ala Lys Ala
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 66

Glu Ala Glu Ala Glu Ala Glu Ala Glu Ala Glu Ala Glu Ala Glu Ala
1               5                   10                  15
```

```
<210> SEQ ID NO 67
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 67

Ala Asp Ala Asp Ala Asp Ala Asp Ala Asp Ala Asp Ala Asp Ala Asp
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 68

Ala Arg Ala Arg Ala Asp Ala Asp Ala Arg Ala Arg Ala Asp Ala Asp
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 69

Val Arg Val Arg Val Asp Val Asp Val Arg Val Arg Val Asp Val Asp
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 70

Ala Arg Ala Asp Ala Arg Ala Asp Ala Arg Ala Asp
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 71

Ala Lys Ala Asp Ala Lys Ala Asp Ala Lys Ala Asp
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 72

Ala His Ala Asp Ala His Ala Asp Ala His Ala Asp
1               5                   10
```

```
-continued

<210> SEQ ID NO 73
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 73

Ala Arg Ala Glu Ala Arg Ala Glu Ala Arg Ala Glu
 1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 74

Ala Lys Ala Glu Ala Lys Ala Glu Ala Lys Ala Glu
 1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 75

Ala His Ala Glu Ala His Ala Glu Ala His Ala Glu
 1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synyhetically generared peptide

<400> SEQUENCE: 76

Arg Ala Arg Ala Arg Ala Asp Ala Asp Ala Asp Ala
 1               5                   10
```

COMPOSITIONS AND METHODS FOR PROMOTING HEMOSTASIS AND OTHER PHYSIOLOGICAL ACTIVITIES

RELATED APPLICATIONS

This application claims the benefit of U.S. application No. 60/674,612, filed Apr. 25, 2005, and U.S. application No. 60/758,827, filed Jan. 13, 2006, the contents of which are hereby incorporated by reference in the present application in their entirety.

GOVERNMENT SUPPORT

The United States government has provided grant support utilized in the development of the present invention (National Institutes of Health grant number EY00126). The United States Government may therefore have certain rights in the invention.

BACKGROUND OF THE INVENTION

Despite the availability of blood products, blood loss is a major cause of morbidity and mortality. There are many causes of such loss, including severe injury and clinical conditions such as the rupture of an aneurysm, esophageal or gastric ulcers, and esophageal varices. A loss of integrity of a major artery can rapidly lead to death, particularly if it occurs in a setting where there is no rapid access to medical care.

Bleeding during surgery is often a major concern. Blood loss can cause a myriad of problems for the patient while the presence of blood in undesirable locations can be detrimental to normal tissue or interfere with the surgeon's ability to view the operative field. The surgery must be delayed while blood is removed and the bleeding is brought under control. Bleeding can be problematic even during minimally invasive surgery (e.g., laparoscopic surgery). In some instances, surgeons must convert these preferred procedures into traditional open surgeries if bleeding cannot be adequately controlled.

Bleeding can also be problematic in diagnostic and interventional procedures that involve the percutaneous introduction of instrumentation into an artery, vein or smaller vessel. For example, procedures such as coronary angioplasty, angiography, atherectomy, and stenting of arteries often involve accessing the vasculature through a catheter placed into a blood vessel such as the femoral artery. Once the procedure is completed and the catheter or other instrument is removed, bleeding from the punctured vessel must be controlled.

Options for controlling bleeding in any of these settings are limited. One of the oldest methods includes application of pressure, either directly to a vessel or to the body external to the vessel. Pressure must be maintained until the bleeding is under control. This procedure is time-consuming and inconvenient, and the patient is at risk of hematoma. Other physical methods include the use of clamps, clips, plugs, sponges, or the like. These devices have limited efficacy, and they can be cumbersome to apply, particularly if there are many small bleeding vessels. Use of heat to coagulate blood and cauterize bleeding vessels is widely used during surgery, but it is a destructive process that can result in damage to collateral tissue. Furthermore, these methods require equipment and expertise and are thus not suitable for use outside of medical settings. In addition to heat and mechanical devices, a variety of compounds have been used to promote hemostasis, but none of these are ideal.

It is therefore an object of the present invention to provide a method and compositions for better controlling leakage of bodily fluids such as blood, interstitial fluid, and cerebrospinal fluid.

It is another object of the present invention to provide such compositions formulated in a variety of ways, including as a bandage, spray, coating, or powder.

It is a still further object of the present invention to provide a composition that can be used to control leakage of bodily fluids but is sufficiently clear that a physician can see and work through the material.

SUMMARY OF THE INVENTION

Compositions including peptides with alternating hydrophilic and hydrophobic monomers that allow them to self-assemble under physiological conditions are formulated for application to wounds. The concentration of the self-assembling peptides in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling peptides can be higher in stock solutions and in solid (e.g., powdered) formulations. Solid preparations may have a concentration of self-assembling peptides approaching 100% (e.g., the concentration of self-assembling peptides can be 95, 96, 97, 98, 99% or more (e.g., 99.99%) of the composition). Whether in liquid or solid form, the peptides can be brought to the desired concentration prior to use by addition of a diluent (e.g., water (e.g., deionized water), fillers, or oil.

The formulations include a pharmaceutically acceptable carrier or are provided as part of a medical device or coating. The formulations may also include other therapeutic, prophylacetic or diagnostic agents. These may be anti-inflammatories, vasoactive agents, anti-infectives, anesthetics, growth factors, and/or cells. Metals may be added as chelators or to decrease adhesion. In one embodiment, the formulation is provided as a dry or lyophilized powder which can be administered directly as a powder or a tablet, disk, or wafer, which hydrates at the site of application, or suspended or dissolved in a liquid, most preferably aqueous, and applied as a spray, paint, or injection or a hydrogel including a material such as chitin, collagen, alginate, or synthetic polymer. In a preferred embodiment, the material is provided in combination with an oil, and forms a laminate. In another embodiment, the formulation is provided as a coating on a device, for example a stent or a catheter, which may be applied by dissolving the self-assembling peptides in an aqueous solution and drying on the device, or mixed with a polymeric carrier and applied to the device. In yet another embodiment, the formulation is provided in a bandage, foam or matrix, in which the peptides may be dispersed or absorbed. The formulation could also be in the form of sutures, tape, or adhesive, or applied to a material such as a surgical drape, to prevent contamination. The material is also useful to isolate tissue, for example, during removal of a specific tissue or tumor, in the eye or lung to prevent hemorrhage (as in response to hemorrhagic fever), for preservation of tissue for subsequent transplantation or reattachment, and as a bulking, stabilizing or hydrating agent. As noted, the material can be used to facilitate removal of a tumor, including a tumor that is difficult to resect due to, for example, its size (as can occur with hepatomas), consistency, or location (e.g., an acoustic neuroma). The methods can include identifying a patient (e.g., a human patient) in need of treatment and providing a composition including self-assembling peptides in the vicinity of the tumor. The amount of the composition used, and the concentration of peptides therein, will be sufficient to allow the composition to form a gel or semi-solid coating or casing around the tumor, a portion thereof, or cells thereof. The surgeon then dissects through the gel surrounding the tumor (or an identified portion thereof) and removes the gel encasing the tumor, the portion thereof, or tumor cells.

In certain embodiments, the material may be useful in a blood stabilizer, since it does not lyse blood and inhibits platelet aggregation. In another embodiment, the materials, at concentrations insufficient for self assembly, can be used to preserve blood.

One or more of the compositions described herein can be assembled in kits, together with instructions for use. For example, the kits can include a biocompatible composition including self-assembling peptides (or a concentrated solution or powdered formulation thereof, together with a diluent) and a vasoconstrictor, a coloring agent, and/or an analgesic or anesthetic agent and instructions for their combination (if not already combined) and use (e.g., dilution and administration). The kits can further include one or more of the additional agents described herein. These agents can be present within a peptide-based composition or packaged separately, and they can include one or more types of biological cells, an antimicrobial (e.g., antibiotic) or other therapeutic, collagen, an anti-inflammatory agent, a growth factor, or a nutrient. The kit may also include one or more of a syringe, a needle, a pipette, gauze, sponges, cotton, swabs, a bandage, a nosebleed plug, a disinfectant, surgical thread, scissors, a scalpel, a sterile fluid, a spray canister, including those in which a liquid solution is sprayed through a simple hand pump, a sterile container, or disposable gloves.

Unless the context dictates otherwise, we intend the terms "composition(s)", "material(s)", and "formulation(s)" to be used interchangeably.

The formulations can be administered as appropriate for treatment of one or more disorders or conditions. For example, the formulations may be applied to repair an injury or during surgery, for example of the lung, eye or dura, or following an epidural or spinal tap, to stop leakage of blood, interstitial fluid, or cerebrospinal fluid. The formulation may be administered to a burn or ulcer, especially when formulated with anesthetics, anti-inflammatories, growth factors, and anti-infectives, in the form of a foam, matrix or bandage, to stop bleeding (any such inhibition may be characterized as a promotion of hemostasis) or loss of interstitial fluid. The formulation may be included in (e.g., dispersed in or coated onto) a suture or adhesive for administration at the time of or as released following suturing or gluing of a wound, thereby limiting bleeding, loss of tissue fluids, or other fluids such as those produced by parenchymal tissues such as the liver, pancreas, and gastrointestinal tract. The formulation may be applied to any site of bleeding in a bandage, gauze, sponge, or other material for immediate control of bleeding, or released later to control bleeding if the initial treatment such as suturing or pressure is insufficient. Dried fabric, dehydrated foams or hydrogels, or bandages containing the formulation may be part of first aid kits for treatment of injuries, for example, in war, at accident sites, or clinics where rapid treatment may be required and storage space is limited. In embodiments featuring bandages or dressings, the bandage or dressing can include a first layer of sufficient shape and size to cover a wound or a substantial portion thereof (e.g., the most injured portion of the tissue or the area bleeding most profusely). The first layer can have a top surface, a bottom surface, and a perimeter that is, optionally, wholly or partially covered with an adhesive. A second layer of the bandage or dressing can be detachably affixed to the bottom surface of the first layer, optionally excluding the perimeter or any part of the perimeter bearing adhesive, and can include a liquid or non-liquid composition (e.g., a gel, paste, foam, cream, ointment, powdered compositions and wafers or disks) including self-assembling peptides. The composition will come in contact with the wound upon application of the bandage or dressing and is transferable from the bandage or dressing to the wound site upon removal of the first layer or the first and second layers. In simpler configurations, the composition including self-assembling molecules can be associated with the bottom of the first layer (e.g., interior to the adhesive perimeter), and the second layer can be omitted. In either case, either the first and/or second layers can include a transparent window, through which some or all of the underlying wound can be viewed. The composition including the self-assembling agent(s) can be added to the bandage before it is packaged or just before use. In another embodiment, the formulation may include a further physical barrier, such as a layer of silicon film, to prevent loss of fluid by drying, after the active flow of fluids has been stopped by application of the formulation. The formulation may be applied as a hydrogel, laminate including oil, or spray.

The liquid formulations may be provided in a syringe or pipette having a barrel containing a composition including self-assembling peptides and a means for expelling the composition from an open tip of the syringe or pipette (e.g., a plunger or bulb). The syringe may consist of one or more compartments, so that mixing of the self-assembling peptides with one or more other agents occurs at the time of application. The compartments may also contain an excipient such as a material that forms a hydrogel or adhesive in one compartment and the self-assembling peptides in the other compartment (respectively, first and second compartments). In another embodiment, one compartment (a first compartment) may contain lyophilized self-assembling peptides or particles of self-assembling peptides, and another compartment (a second compartment) may contain solution to dissolve or hydrate the peptides. The composition within the barrel can further include a therapeutic, prophylacetic or diagnostic agent or coloring agent, or any other non-fibrous agent described herein. The compartments of the syringe can be joined at a common end by a y-junction to allow simultaneous dispensing and mixing of the compositions, materials, or formulations within each compartment and the plunger or other device used to expel the compositions can be suitably configured to accommodate the compartments.

DETAILED DESCRIPTION

Figure 1:
FIG. 1 shows the sequence of a representative self-assembling peptide, RADA16-I (SEQ ID NO: 1), and a space-filling model illustrating the repeating structure and approximate scale.
Figure 1:
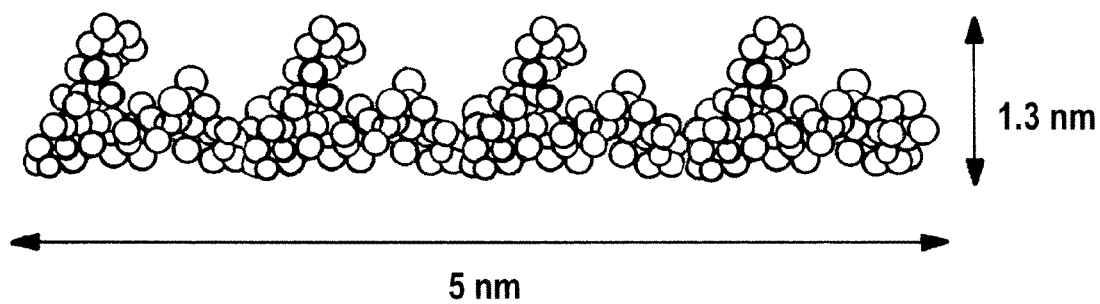

I. Formulations.

A. Self-Assembling Peptides

The term "peptide," as used herein includes "polypeptide," "oligopeptide," and "protein," and refers to a string of at least two α-amino acid residues linked together by covalent bonds (e.g., peptide bonds). Useful peptides can vary in length so long as they retain the ability to self-assemble to an extent useful for one or more of the purposes described herein. Peptides having as few as two α-amino acid residues or as many as approximately 200 residues may be suitable, and those recognized to self-assemble typically have a length within this range (e.g., 8-200, 8-36, 8-24, 8-16, 12-20, 6-64, or 16-20 amino acid residues). Depending on the context, "peptide" may refer to an individual peptide or to a collection of peptides having the same or different sequences, any of which may contain only naturally occurring α-amino acid residues, non-naturally occurring α-amino acid residues, or both. α-Amino acid analogs are also known in the art and may alternatively be employed. In particular, α-amino acid residues of the D-form may be used. In addition, one or more of the amino acid residues in a self-assembling peptide can be altered or derivatized by the addition of a chemical entity such as an acyl group, a carbohydrate group, a carbohydrate chain, a phosphate group, a farnesyl group, an isofarnesyl group, a fatty acid group, or a linker for conjugation or functionalization. Useful peptides can also be branched, in which case they will contain at least two amino acid polymers, each of which consists of at least three amino acid residues joined by peptide bonds. The two amino acid polymers themselves are linked, but not by a peptide bond.

While the sequences of the peptides can vary, useful sequences include those that convey an amphiphilic nature to the peptides (e.g., the peptides can include approximately equal numbers of hydrophobic and hydrophilic amino acid residues), and the peptides can be complementary and structurally compatible. Complementary peptides have an ability to interact through ionic or hydrogen bonds that form between residues (e.g., hydrophilic residues) on adjacent peptides in a structure. For example, a given hydrophilic residue in a peptide can either hydrogen bond or ionically pair with a hydrophilic residue on an adjacent peptide. Unpaired residues can be exposed to the solvent. Peptide-peptide interaction may also involve van der Waals forces or other forces that do not constitute covalent bonds. The peptides are structurally compatible when they are capable of maintaining a sufficiently constant intrapeptide distance to allow assembly and structure formation. While the intrapeptide distance can vary, it can be quite small (e.g., less than about 4, 3, 2, or 1 Å). The intrapeptide distance (e.g., an average of a representative number of distances) can be larger than this, however. These distances can be calculated based on molecular modeling or based on a simplified procedure that has been previously reported (see U.S. Pat. No. 5,670,483).

More specifically, the peptides can have, or can include, a sequence of amino acid residues conforming to one or more of Formulas I-IV:

$$((Xaa^{neu}\text{-}Xaa^+)_x(Xaa^{neu}\text{-}Xaa^-)_y)_n \quad (I)$$

$$((Xaa^{neu}\text{-}Xaa^-)_x(Xaa^{neu}\text{-}Xaa^+)_y)_n \quad (II)$$

$$((Xaa^+\text{-}Xaa^{neu})_x(Xaa^-\text{-}Xaa^{neu})_y)_n \quad (III)$$

$$((Xaa^-\text{-}Xaa^{neu})_x(Xaa^+\text{-}Xaa^{neu})_y)_n \quad (IV)$$

where: $Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2 or 4, independently; and n is an integer having a value of 1-10 (e.g., 1-8, 1-5, or 1-3).

The self-assembling peptides can have sequence of amino acid residues where $Xaa^{neu}$ represents alanine, valine, leucine, isoleucine, or glycine; $Xaa^+$ represents arginine, lysine or histidine; and $Xaa^-$ represents aspartic acid or glutamic acid. For example, the self-assembling peptides can have, or can include, the amino acid sequence RADARADARADA (SEQ ID No:31). Other examples include ARADARADARAD (SEQ ID NO:70); AKADAKADKAD (SEQ ID NO:71); AHADAHADAHAD (SEQ ID NO:72); ARAEARAEARAE (SEQ ID NO:73); AKAEAKAEAKAE (SEQ ID NO:74); and AHAEAHAEAHAE (SEQ ID NO:75).

The structures described herein can be formed through self-assembly of the peptides described in U.S. Pat. Nos. 5,670,483; 5,955,343; 6,548,630; and 6,800,481 and in Holmes et al., *Proc. Natl. Acad. Sci. USA*, 97:6728-6733 (2000); Zhang et al., *Proc. Natl. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 9:297-312 (1998); and Caplan et al., *Biomacromolecules*, 1:627-631 (2000). Representative self-assembling peptides are shown in Table 1.

TABLE 1

Representative Self-Assembling Peptides

| Name | Sequence (n-->c) | Modulus | |
|---|---|---|---|
| RADA16-I | n-RADARADARADARADA-c | I | (SEQ ID NO: 1) |
| RGDA16-I | n-RADARGDARADARGDA-c | I | (SEQ ID NO: 2) |
| RADA8-I | n-RADARADA-c | I | (SEQ ID NO: 3) |
| RAD16-II | n-RARADADARARADADA-c | II | (SEQ ID NO: 4) |
| RAD8-II | n-RARADADA-c | II | (SEQ ID NO: 5) |
| EAKA16-I | n-AEAKAEAKAEAKAEAK-c | I | (SEQ ID NO: 6) |
| EAKA8-I | n-AEAKAEAK-c | I | (SEQ ID NO: 7) |
| RAEA16-I | n-RAEARAEARAEARAEA-c | I | (SEQ ID NO: 8) |
| RAEA8-I | n-RAEARAEA-c | I | (SEQ ID NO: 9) |
| KADA16-I | n-KADAKADAKADAKADA-c | I | (SEQ ID NO: 10) |
| KADA8-I | n-KADAKADA-c | I | (SEQ ID NO: 11) |
| EAH16-II | n-AEAEAHAHAEAEAHAH-c | II | (SEQ ID NO: 12) |
| EAH8-II | n-AEAEAHAH-c | II | (SEQ ID NO: 13) |
| EFK16-II | n-FEFEFKFKFEFEFKFK-c | II | (SEQ ID NO: 14) |
| EFK8-II | n-FEFKFEFK-c | I | (SEQ ID NO: 15) |
| ELK16-II | n-LELELKLKLELELKLK-c | II | (SEQ ID NO: 16) |
| ELK8-II | n-LELELKLK-c | II | (SEQ ID NO: 17) |
| EAK16-II | n-AEAEAKAKAEAEAKAK-c | II | (SEQ ID NO: 18) |

TABLE 1-continued

Representative Self-Assembling Peptides

| Name | Sequence (n-->c) | Modulus | |
|---|---|---|---|
| EAK12 | n-AEAEAEAEAKAK-c | IV/II | (SEQ ID NO: 19) |
| EAK8-II | n-AEAEAKAK-c | II | (SEQ ID NO: 20) |
| KAE16-IV | n-KAKAKAKAEAEAEAEA-c | IV | (SEQ ID NO: 21) |
| EAK16-IV | n-AEAEAEAEAKAKAKAK-c | IV | (SEQ ID NO: 22) |
| RAD16-IV | n-RARARARADADADADA-c | IV | (SEQ ID NO: 23) |
| DAR16-IV | n-ADADADADARARARAR-c | IV | (SEQ ID NO: 24) |
| DAR16-IV* | n-DADADADARARARARA-c | IV | (SEQ ID NO: 25) |
| DAR32-IV | n-(ADADADADARARARAR)-c | IV | (SEQ ID NO: 26) |
| EHK16 | n-HEHEHKHKHEHEHKHK-c | N/A | (SEQ ID NO: 27) |
| EHK8-I | n-HEHEHKHK-c | N/A | (SEQ ID NO: 28) |
| VE20* | n-VEVEVEVEVEVEVEVEVEVE-c | N/A | (SEQ ID NO: 29) |
| RF20* | n-RFRFRFRFRFRFRFRFRFRF-c | N/A | (SEQ ID NO: 30) |
| RAD12-I | n-RADARADARADA-c | I | (SEQ ID NO: 31) |
| | n-AKAKAEAEAKAKAEAE-c | | (SEQ ID NO: 32) |
| | n-AKAEAKAEAKAEAKAE-c | | (SEQ ID NO: 33) |
| | n-EAKAEAKAEAKAEAKA-c | | (SEQ ID NO: 34) |
| | n-KAEAKAEAKAEAKAEA-c | | (SEQ ID NO: 35) |
| | n-ADADARARADADARAR-c | | (SEQ ID NO: 36) |
| | n-ARADARADARADARAD-c | | (SEQ ID NO: 37) |
| | n-DARADARADARADARA-c | | (SEQ ID NO: 38) |
| | n-ADARADARADARADAR-c | | (SEQ ID NO: 39) |
| | n-ARADAKAEARADAKAE-c | | (SEQ ID NO: 40) |
| | n-AKAEARADAKAEARAD-c | | (SEQ ID NO: 41) |
| | n-ARAKADAEARAKADAE-c | | (SEQ ID NO: 42) |
| | n-AKARAEADAKARADAE-c | | (SEQ ID NO: 43) |
| | n-AQAQAQAQAQAQAQAQ-c | | (SEQ ID NO: 44) |
| | n-VQVQVQVQVQVQVQVQ-c | | (SEQ ID NO: 45) |
| | n-YQYQYQYQYQYQYQYQ-c | | (SEQ ID NO: 46) |
| | n-HQHQHQHQHQHQHQHQ-c | | (SEQ ID NO: 47) |
| | n-ANANANANANANANAN-c | | (SEQ ID NO: 48) |
| | n-VNVNVNVNVNVNVNVN-c | | (SEQ ID NO: 49) |
| | n-YNYNYNYNYNYNYNYN-c | | (SEQ ID NO: 50) |
| | n-HNHNHNHNHNHNHNHN-c | | (SEQ ID NO: 51) |
| | n-ANAQANAQANAQANAQ-c | | (SEQ ID NO: 52) |
| | n-AQANAQANAQANAQAN-c | | (SEQ ID NO: 53) |
| | n-VNVQVNVQVNVQVNVQ-c | | (SEQ ID NO: 54) |
| | n-VQVNVQVNVQVNVQVN-c | | (SEQ ID NO: 55) |
| | n-YNYQYNYQYNYQYNYQ-c | | (SEQ ID NO: 56) |
| | n-YQYNYQYNYQYNYQYN-c | | (SEQ ID NO: 57) |
| | n-HNHQHNHQHNHQHNHQ-c | | (SEQ ID NO: 58) |
| | n-HQHNHQHNHQHNHQHN-c | | (SEQ ID NO: 59) |
| | n-AKAQADAKAQADAKAQAD-c | | (SEQ ID NO: 60) |
| | n-VKVQVDVKVQVDVKVQVD-c | | (SEQ ID NO: 61) |
| | n-YKYQYDYKYQYDYKYQYD-c | | (SEQ ID NO: 62) |
| | n-HKHQHDHKHQHDHKHQHD-c | | (SEQ ID NO: 63) |
| | n-ADADAKAKADADAKAK-c | | (SEQ ID NO: 64) |
| | n-KAKAKAKAKAKAKAKA-c | | (SEQ ID NO: 65) |
| | n-EAEAEAEAEAEAEAEA-c | | (SEQ ID NO: 66) |
| | n-ADADADADADADADAD-c | | (SEQ ID NO: 67) |
| | n-ARARADADARARADAD-c | | (SEQ ID NO: 68) |

TABLE 1-continued

Representative Self-Assembling Peptides

| Name | Sequence (n-->c) | Modulus |
|---|---|---|
| | n-VRVRVDVDVRVRVDVD-c | (SEQ ID NO: 69) |

N/A denotes not applicable
*These peptides form a β-sheet when incubated in a solution containing NaCl, however they have not been observed to self-assemble to form macroscopic structures.

Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another by the formation of disulfide bonds. Structures bonded in this manner may have increased mechanical strength relative to structures made with comparable peptides that do not include cysteine residues.

The amino acid residues in the self-assembling peptides can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrrolysine or selenocysteine). Non-naturally occurring amino acids have not been found in nature, but can be incorporated into a peptide chain. These include D-alloisoleucine(2R,3S)-2-amino-3-methylpentanoic acid, L-cyclopentyl glycine (S)-2-amino-2-cyclopentyl acetic acid. For other examples, one can consult textbooks or the worldwide web (a site is maintained by the California Institute of Technology and displays structures of non-natural amino acids that have been successfully incorporated into functional proteins). Non-natural amino acid residues and amino acid derivatives listed in U.S. Application No. 20040204561 (see ¶ 0042, for example) can be used. Self-assembling peptides can be chemically synthesized or purified from natural or recombinantly-produced sources by methods well known in the art. For example, peptides can be synthesized using standard f-moc chemistry and purified using high pressure liquid chromatography (HPLC).

Where self-assembling peptides are used, it is thought that their side-chains (or R groups) partition into two faces, a polar face with positively and/or negatively charged ionic side chains, and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides may therefore be called ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residue alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV." A peptide having four repeating units of the sequence EAKA may be designated EAKA16-I, and peptides having other sequences may be described by the same convention.

Self-complementary peptides such as EAKA16-I, RADA16-I, RAEA16-I, and KADA16-I are described in Table 1. Peptides with modulus I (i.e., peptides having alternate positively and negatively charged R groups on one side (e.g., the polar face) of the β-sheet) are described by each of Formulas I-IV, where x and y are 1. Peptides of modulus II (i.e., peptides having two residues bearing one type of charge (e.g., a positive charge) followed by two residues bearing another type of charge (e.g., a negative charge) are described by the same formulas where both x and y are 2. Peptides of modulus III have (i.e. peptides having three residues bearing one type of charge (e.g., a positive charge) followed by three residues hearing another type of charge (e.g., a negative charge) such as RARARADADADA (SEQ ID NO:76).

Modulus IV ionic self-complementary peptides containing 16 amino acids; such as EAK16-IV, KAE16-IV, DAR16-IV, and RAD16-IV have also been studied. If the charged residues in these self-assembling peptides are substituted (e.g., the positively charged lysines are replaced by positively charged arginines and the negatively charged glutamates are replaced by negatively charged aspartates), there are essentially no known significant effects on the self-assembly process. However, if the positively charged residues (lysine and arginine) are replaced by negatively charged residues (aspartate and glutamate), the peptides can no longer undergo self-assembly to form macroscopic structures. However, they can still form a beta-sheet structure in the presence of a salt. Other hydrophilic residues that form hydrogen bonds, such as asparagine and glutamine, may be incorporated into the peptides instead of, or in addition to, charged residues. If the alanine residues in the peptides are changed to more hydrophobic residues, such as leucine, isoleucine, phenylalanine or tyrosine, the resulting peptides have a greater tendency to self-assemble and form peptide matrices with enhanced strength. Some peptides that have similar amino acids compositions and lengths as the peptides described here form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays.

Peptide-based structures can be formed of heterogeneous mixtures of peptides (i.e., mixtures containing more than one type of peptide conforming to a given formula or to two or more of the formulas). In some embodiments, each of the types of peptides in the mixture is able to self-assemble alone. In other embodiments, one or more of each type of peptide would not alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides which are complementary and structurally compatible to each other, can be used. For example, mixtures of KAKAKAKAKAKAKAKA (SEQ ID NO:65) and EAEAEAEAEAEAEAEA (SEQ ID NO:16) or of KAKAKAKAKAKAKAKA (SEQ ID NO:65) and ADADADADADADADAD (SEQ ID NO 67) would be expected to form membranes, but not any of these peptides alone due to lack of complementarity.

The compositions described herein (regardless of the precise form (e.g., whether in a liquid form or molded) and regardless of the overall compositions (e.g., whether combined with another agent, contained within a device, or packaged in a kit) can include a mixture of RADA16-I (SEQ ID NO:1) or RADA12-I and EAKA16-I (SEQ ID NO:6) or EAK16-II (SEQ ID NO:18). Other mixtures can include RAD16-II (SEQ ID NO:4) or RAD12-II and EAKA16-I (SEQ ID NO:6) or EAK16-II (SEQ ID NO:18). Other mixtures can include various lengths of the same peptide sequence or mixtures of modulus I and modulus II peptides. For example, one could use a mixture of RADA12-I and RADA12-II; of RADA16-I and RADA16-II; of RADA12-I and RADA16-I; of RADA12-II and RADA16-II; of EAKA12-I and EAKA12-II; of EAKA16-I and EAKA16-II; of EAKA12-I and EAKA16-II; or of EAKA12-II and EAKA16-II. Use of a mixture rather than a single peptide can modulate properties such as the speed of assembly and the stiffness of the assembled material.

In summary, peptides useful in the manner described herein can have, or can include, a sequence of alternating hydrophobic and hydrophilic amino acid residues that are complementary and structurally compatible. As noted, the peptides can vary in length and can be a multiple of four residues, but does not have to be. For example, the peptides can be at least eight amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. The amino acid residues can be selected from D-amino acids or L-amino acids, and the peptides or mixtures of peptides can include combinations thereof. Suitable, naturally-occurring hydrophobic amino acid residues include Ala, Val, Ile, Met, Phe, Tyr, Trp, Ser, Thr and Gly. The hydrophilic amino acid residues can be basic amino acids (e.g., Lys, Arg, His, Orn); acidic amino acids (e.g., Glu, Asp); or amino acids that form hydrogen bonds (e.g., Asn, Gln). If L-amino acids are present in the structure, degradation produces amino acids that may be reused by the host tissue. The fact that L-configured amino acid residues occur naturally within the body distinguishes this class of compounds from numerous other biocompatible substances and may offer unique advantages.

Either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group ($NH_2$) can be used to neutralize an "extra" negative charge that may otherwise be present at the C-terminus (e.g., a charge not resulting from the side chain of the C-terminal amino acid residue). Where an amine is used, the C-terminus would bear an amide (—$CONH_2$). The neutralization of charges on a terminus may facilitate self-assembly. One of ordinary skill in the art will be able to select other suitable groups.

Self-assembled structures can be formed that have varying degrees of stiffness or elasticity. The structures typically have a low elastic modulus (e.g., a modulus in the range of 1-10 kPa as measured by standard methods, such as in a standard cone-plate rheometer). Low values may be preferable, as they permit structure deformation as a result of movement, in response to pressure, in the event of cell contraction. More specifically, stiffness can be controlled in a variety of ways, including by changing the length, sequence, and/or concentration of the precursor molecules (e.g., self-assembling peptides). Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are within the scope of the present invention. For example, amino acid residues with aromatic rings may be incorporated and cross-linked by exposure to uv light. The extent of crosslinking can be precisely controlled by applying the radiation for a predetermined length of time to peptides of known sequence and concentration. The extent of crosslinking can be determined by light scattering, gel filtration, or scanning electron microscopy using standard methods. Furthermore, crosslinking can be examined by HPLC or mass spectrometry analysis of the structure after digestion with a protease, such as matrix metalloproteases. Material strength may be determined before and after cross-linking. Regardless of whether cross-linking is achieved by a chemical agent or light energy, the molecules may be cross-linked in the course of creating a mold or when peptide-containing solutions are applied to the body.

The half-life (e.g., the in vivo half-life) of the structures can also be modulated by incorporating protease or peptidase cleavage sites into the precursors that subsequently form a given structure. Proteases or peptidases that occur naturally in vivo or that are introduced (e.g., by a surgeon) can then promote degradation by cleaving their cognate substrates. Combinations of any of the modifications described here can be made. For example, self-assembling peptides that include a protease cleavage site and a cysteine residue and/or a cross-linking agent, kits and devices containing them, and methods of using them can be utilized.

FIG. 1 shows the sequence of a representative self-assembling peptide, RADA16-I, and a space-filling model showing the repeating structure and approximate scale. Interwoven nanofibers and individual nanofibers are observed upon microscopic examination of the materials formed by peptide self-assembly. Gel-like structures formed following peptide self-assembly appeared transparent and flexible.

The peptide structures formed from any self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

B. Formation of Self-Assembling Peptide Materials

Prior to self-assembly the peptides may be contained in (e.g., dissolved in) a solution that is substantially free of ions (e.g., monovalent ions) or that contains a sufficiently low concentration of ions to prevent significant self-assembly (e.g., a concentration of ions less than 10, 5, 1, or 0.1 mM). Self-assembly may be initiated or enhanced at any subsequent time by the addition of an ionic solute or diluent to a peptide solution or by a change in pH. For example, NaCl at a concentration of between approximately 5 mM and 5 M will induce the assembly of macroscopic structures within a short period of time (e.g., within a few minutes). Lower concentrations of NaCl may also induce assembly but at a slower rate. Alternatively, self-assembly may be initiated or enhanced by introducing the peptides (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure) comprising such ions. Generally, self-assembly is expected to occur upon contacting the peptides with such a solution in any manner.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$, and the concentration of such ions required to induce or enhance self-assembly is typically at least 5 mM (e.g., at least 10, 20, or 50 mM). Lower concentrations also facilitate assembly, though at a reduced rate. When desired, self-assembling peptides can be delivered with a hydrophobic material (e.g. a pharmaceutically acceptable oil) in a concentration that permits self-assembly, but at a reduced rate. When self-assembling peptides are mixed with a hydrophobic agent such as an oil or lipid the assembly of the material forms different structures. The structures will appear like ice on a layer of oil but in some cases when another material is added, the material will assemble into various other three dimensional structures that may be suitable for drug loading or other relevant therapeutic agents. The hydrophilic part of the molecule will assemble in such a way to minimize hydrophobic-hydrophilic interaction, thereby creating a barrier between the two environments. Several experiments have shown that the self-assembling peptides will align on the surface of the oil like ice on water with the hydrophobic part of the molecule toward the surface and the hydrophilic portion of the molecule facing away from the oil, or will form toroidal like structures with the hydrophobic material contained inside. This type of behavior enables the encapsulation of therapeutics or other molecule of interested for delivery in the body.

Depending on the formulation and desired properties of the macroscopic structure (e.g., the stiffness of the scaffold or the rate of its formation), the concentration of precursors (e.g., self-assembling peptides) can vary from approximately 0.01% w/v (0.1 mg/ml) to approximately 99.99% w/v (999.9 mg/ml), inclusive. For example, the concentration prior to scaffold formation can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). In some embodiments, the concentration can also be less than 0.1%. The precursors (e.g., self-assembling peptides) can be formulated as powders and administered in a powder form or resuspended. If dry, the peptides can then self-assemble following contact with bodily fluids (e.g., at a site of injury).

Peptide-based structures can be formed within regularly or irregularly-shaped molds, which may include a body cavity or a portion of the body (e.g., the lumen of a blood vessel) or which may be an inert material such as plastic or glass. The structures or scaffolds can be made to conform to a predetermined shape or to have a predetermined volume. To form a structure with a predetermined shape or volume (e.g., a desired geometry or dimension, including thin sheets or films), an aqueous peptide solution is placed in a pre-shaped casting mold, and the peptides are induced to self-assemble by the addition of a plurality of ions. Alternatively, the ions may be added to the peptide solution shortly before placing the solution into the mold, provided that care is taken to place the solution into the mold before substantial assembly occurs. Where the mold is a tissue (e.g., the lumen of a blood vessel or other compartment, whether in situ or not), the addition of an ionic solution may not be necessary. The resulting material characteristics, the time required for assembly, and the dimensions of the macroscopic structure that forms are governed by the concentration and amount of peptide solution that is applied, the concentration of ions used to induce assembly of the structure, and the dimensions of the casting apparatus. The scaffold can achieve a gel-like or substantially solid form at room temperature, and heat may be applied to facilitate the molding (e.g., one can heat a solution used in the molding process (e.g., a precursor-containing solution) to a temperature ranging up to about body temperature (approximately 37° C.)). Once the scaffold has reached the desired degree of firmness, it can be removed from the mold and used for a purpose described herein.

Materials that assemble and/or undergo a phase transition (e.g., a transition from a liquid state to a semi-solid, gel, etc.) when they come in contact with the body are useful in preventing the movement of bodily substances. In the case of skin, the compositions may be administered with an ionic solution or oil in order to self assemble, in the absence of moisture or oil on the skin. Self-assembly or phase transition is triggered by components found in a subject's body (e.g., ions) or by physiological pH and is assisted by physiological temperatures. Self-assembly or phase transition can begin when the compositions are exposed to or brought into contact with a subject's body and may be facilitated by the local application of heat to the area where the composition has been (or will be) deposited. The subject, for any indication described herein, can be a human. Based on studies to date, self-assembly occurs rapidly upon contact with internal bodily tissues without the application of additional heat. In one embodiment, the time required for effective assembly and/or phase transition can be 60 seconds or less following contact with a subject's internal tissues or to conditions similar to those found within the body (e.g., in 50, 40, 30, 20, or 10 seconds or less). In some circumstances, such as where the concentration of self-assembling agents in the composition is low or where the movement of the bodily substance is substantial, self-assembly or phase transition may take longer to achieve the desired effect, for example, up to a minute, 5 minutes, 10 minutes, 30 minutes, an hour, or longer. For example, a solution containing a self-assembling peptide applied to sites of blood vessel transection in the brain, liver, or muscle provided complete hemostasis within times as short as 10 seconds following application (see Examples 1-3). Ion-containing solutions may be preferred when the compositions are used to protect a subject from contamination, as phase transitions do not occur, or do not readily occur, when non-ionic compositions contact intact skin.

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance in a subject in need thereof. Self-assembly can also be achieved ex vivo by exposure to conditions within a certain range of physiological values (e.g., conditions appropriate for cell or tissue culture). While liquid formulations are readily dispensed, the compositions administered may also be in a gel form that may become stiffer upon contact with the subject's body.

In one embodiment, the concentration of the self-assembling peptides in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling peptides can be higher in stock solutions and in solid (e.g., powdered) formulations. In solid preparations, the concentration of self-assembling peptides can approach 100% (e.g., the concentration of self-assembling peptides can be 95, 96, 97, 98, 99% or more (e.g., 99.99%) of the composition). Whether in liquid or solid form, the peptides can be brought to the desired concentration prior to use by addition of a diluent (e.g., deionized water), powder, wetting agent, or a therapeutic, diagnostic or prophylacetic agent.

Regardless of the precise nature of the self-assembling agents, upon exposure to conditions such as those described herein, the agents can form membranous two- or three-dimensional structures including a stable macroscopic porous matrix having ordered interwoven nanofibers (e.g., fibers approximately 10-20 nm in diameter, with a pore size of about 50-100 nm in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling peptides can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling agents (e.g., peptides) therein. The sequences, characteristics, and properties of the peptides and the structures formed by them upon self-assembly are discussed further below.

The compositions can be formulated as concentrated stocks or in dry form, and these can be diluted or dissolved to form compositions (e.g., biocompatible compositions), which are substantially non-toxic to biological cells in vitro or in vivo. For example, the compositions can contain materials in quantities that do not elicit a significant deleterious effect on the recipient's body (e.g., a prohibitively severe immunological or inflammatory reaction, or unacceptable scar tissue formation).

When a solution containing non-assembled peptides is laid down on a biological tissue, the peptides having sufficient proximity to the tissue assemble, causing the solution to gel. Any solution that remains distant from the tissue remains liquid, as the self-assembling peptides have not yet been exposed to conditions that promote their assembly. As the material is disturbed (e.g., by performing a surgical procedure), liquid material appears to gel as it comes into sufficient contact with the body. At times, the compositions can take on characteristics ranging from a liquid to those of a solid, appearing gel- or salve-like or as a slurry).

B. Additional Therapeutic, Prophylacetic and Diagnostic Agents

The formulations typically include an excipient or other pharmaceutically acceptable carrier or are provided as part of a medical device or coating. The formulations may also include other therapeutic, prophylacetic or diagnostic agents. In a preferred embodiment, these agents may be anti-inflammatories, vasoactive agents, anti-infectives, anesthetics, growth factors, and/or cells.

These agents can also be peptides or proteins, polysaccharides or saccharides, nucleic acids or nucleotides, proteoglycans, lipids, carbohydrates, or a small molecule, typically an organic compound having multiple carbon-carbon bonds, that may be isolated from nature or created via chemical synthesis. Small molecules have relatively low molecular weights (e.g., less than about 1500 g/mol) and are not peptides or nucleic acids. The substance can also be a biomolecule, which includes molecules such as a peptide, proteoglycan, lipid, carbohydrate, or nucleic acid, any of which may have characteristics typical of such molecules found in living organisms. Like small molecules, biomolecules can be naturally occurring or may be artificial (i.e., they may be molecules that have not been found in nature). For example, a protein having a sequence that has not been found in nature (e.g., one that does not occur in a publicly available database of sequences) or that has a known sequence modified in an unnatural way by a human hand (e.g., a sequence modified by altering a post-translational process such as glycosylation) is an artificial biomolecule. Nucleic acid molecules encoding such proteins (e.g., an oligonucleotide, optionally contained within an expression vector) are also biomolecules and can be incorporated into the compositions described herein. For example, a composition can include a plurality of self-assembling peptides and cells that express, or that are engineered to express, a protein biomolecule (by virtue of containing a nucleic acid sequence that encodes the protein biomolecule).

Many different therapeutic, prophylactic or diagnostic agents can be incorporated into the formulations. Representative vasoconstrictors, any of which can be formulated with one or more self-assembling peptides (e.g., in a biocompatible composition in liquid, powder or gel form) include epinephrine and phenylephrine; representative coloring agents include arsenazo III, chlorophosphonazo III, antipyrylazo III, murexide, Eriochrome Black T, Eriochrome Blue SE, oxyacetazo I, carboxyazo III, tropolone, methylthymol blue, and Mordant Black 32; representative anesthetic agents include benzocaine, bupivacaine, butamben picrate, chloroprocaine, cocaine, curare, dibucaine, dyclonine, etidocaine, lidocaine, mepivacaine, pramoxine, prilocalne, procaine, propoxycaine, ropivacaine, tetracaine, or combinations thereof. Local application of the anesthetic agent may be all that is required in some situations, for example, for a burn or other wound to the skin, including decubitus ulcers, or for minimally invasive surgeries. Combining local anesthetics with the self-assembling peptides, whether combined by virtue of being present in the same formulation or by virtue of co-administration, can help contain the anesthetic within the body and reduce the amount entering the circulation. Vasoconstrictors such as phenylephrine can be included to prolong the effect of local anesthesia (e.g., 0.1-0.5% phenylephrine). Analgesic agents other than a local anesthetic agent, such as steroids, non-steroidal anti-inflammatory agents like indomethacin, platelet activating factor (PAF) inhibitors such as lexipafant, CV 3988, and/or PAF receptor inhibitors such as SRI 63-441. An anti-infective or antimicrobial agent (e.g., an antibiotic, antibacterial, antiviral, or antifungal agent) can be included for either systemic or local administration. Examples include β-lactam antibiotics such as penicillins and cephalosporins and other inhibitors of cell wall synthesis such as vancomycin, chloramphenicol, tetracyclines, macrolides, clindamyin, streptogramins, aminoglycosides, spectinomycin, sulfonamides, trimethoprim, quinolones, amphotericin B, flucytosine, azoles such as ketoconazole, itraconazole, fluconazole, clotrimazole, and miconazole, griseofulvin, terbinafine, and nystatin. The antimicrobial can be topically administered (e.g., to treat skin infections or burns, or to help prevent infection at a site of catheter insertion (e.g., an intravenous catheter), for example, kanamycin, neomycin, bacitracin, polymixin, topical sulfonamides such as mafenide acetate or silver sulfadiazine, or gentamicin sulfate. The antimicrobial can also be a broad spectrum agent. For example, a second, third, or fourth generation cephalosporin can be used. These agents may be active against a wide range of bacteria including both gram positive and gram negative species. Such antibacterial agents may be particularly appropriate where the present scaffolds are used to inhibit movement of intestinal contents such as during intestinal resection or other surgery that purposefully or accidentally disturbs the integrity of the intestinal wall. One of ordinary skill in the art will be able to select appropriate antimicrobial agents by considering factors such as the patient's history (e.g., any history of an allergic reaction to such agents), the location to which the peptides are to be applied, the type of infectious agent likely to be present, and so forth.

Any of the compositions described herein, whether they contain only self-assembling precursors or precursors and one or more bioactive molecules (e.g., a vasoconstrictor or anesthetic agent) (and whether in a liquid, semi-solid, or solid form), can include a coloring agent. Suitable coloring agents include commercially available food colorings, natural and synthetic dyes, and fluorescent molecules. Preferably, the coloring agent is nontoxic or is included at such low concentrations as to minimize any undesirable effect (e.g., a toxic effect). The use of a coloring agent allows for improved visualization of an area that is covered by a structure or scaffold and can facilitate removal, if such removal is desired. The coloring agent can be one that changes color when it comes into contact with a contaminated area (e.g., a color change may be triggered by the contamination itself (e.g., by the blood or bacteria present at a wound site)). For example, a metabolic product of a bacterium may trigger a color change. Conditions such as pH or redox state induced by contaminants may also be detected. Exemplary indicators include arsenazo III, chlorophosphonazo III, antipyrylazo III, murexide, Eriochrome Black T and Eriochrome Blue SE for $Mg^{2+}$, oxyacetazo I, carboxyazo III, tropolone, methylthymol blue, and Mordant Black 32. AlamarBlue, a redox indicator, and phenol red are also of use in the compositions and methods.

Many other active agents can be included in the compositions. For example, a number of growth factors can be included to accelerate one or more aspects of healing (e.g., angiogenesis, cell migration, process extension, and cell proliferation). These types of compositions can be "included" as others can, by virtue of inclusion in the compositions or by virtue of co-administration in the present methods. Examples include vascular endothelial growth factor (VEGF), a transforming growth factor (TGF) such as transforming growth factor β, a platelet derived growth factor (PDGF), an epidermal growth factor (EGF), a nerve growth factor (NGF), an insulin-like growth factor (e.g., insulin-like growth factor I), a glial growth factor (GGF), a fibroblast growth factor (FGF), etc. It will be appreciated that in many cases these terms refer to a variety of different molecular species. For example, several transforming growth factor β species are known in the art. One of ordinary skill in the art will be guided in the selection of an appropriate growth factor by considering, for example, the site at which the composition is to be administered. For example, an EGF can be included in compositions applied to the skin; an NGF and/or GGF can be included in compositions applied to nerves or the nervous system; and so forth.

The growth factor or another agent can be a chemotactic substance, which has the ability, in vivo or in cell culture, to recruit cells to a site at which the substance is present. The cells recruited may have the potential to contribute to the formation of new tissue or to repair existing, damaged tissue (e.g., by contributing structurally and/or functionally to the tissue (e.g., by providing growth factors or contributing to a desirable immune response)). Certain chemotactic substances can also function as proliferation agents (e.g., neurotropic factors such as NGF or BDNF).

The compositions can also be used in combination with or instead of compounds including, but not limited to, cyanoacrylates, oxidized cellulose, fibrin sealants, collagen gel, thrombin powder, microporous polysaccharide powders, clotting factors (e.g., Factor V, Factor VIII, fibrinogen, or prothrombin) and zeolite powders.

It will be understood that therapeutic molecules are generally administered in an effective amount in order to achieve a clinically significant result, and effective dosages and concentrations are known in the art. These dosages and concentrations can guide the selection of dosages and concentrations in the present context. Bioactive molecules can be provided at a variety of suitable concentrations and in suitable amounts (e.g., in the microgram or milligram range, or greater). For guidance, one can consult texts such as Goodman and Gilman's *The Pharmacological Basis of Therapeutics*, 10th Ed., and Katzung, *Basic and Clinical Pharmacology*.

Cells

Where cells are delivered to a patient (e.g., to promote tissue healing), autologous cells can be used. In one embodiment, the cells could be the use of hematopoietic cells from the patient, dispersed in the material and implanted. In another embodiment, the cells can be cord red blood cells.

Molded scaffolds as described above, liquid compositions, gels, solid (e.g. powders) or semi-solid embodiments may include one or more additional substances such as bioactive molecules or cells. In some instances, the cell may secrete the bioactive molecule either naturally or following genetic engineering (e.g., to express and/or secrete a recombinant protein). The structures (e.g., peptide-based structures) described herein are able to support cell attachment, viability, and growth; these have been observed when cells are cultured on the surface of a peptide-based structure or when cells grow within the material (e.g., when encapsulated). In addition, the structures are able to serve as substrates for neurite growth and synapse formation when neurons are grown on or within them. Thus, bioactive molecules and cells can be encapsulated within the peptide structures and maintain substantial function and viability when so encapsulated (see, e.g., U.S. Ser. Nos. 09/778,200 and 10/196,942).

C. Excipients, Carriers, and Devices

The formulations include a pharmaceutically acceptable carrier or are provided as part of a medical device or coating. The formulations may also include other therapeutic, prophylacetic or diagnostic agents.

In one embodiment, the formulation is provided as a dry or lyophilized powder which can be administered directly as a powder which hydrates at the site of application, or suspended or dissolved in a liquid, most preferably aqueous, and applied as a spray, paint, or injection or a hydrogel such as chitin, collagen, alginate, or synthetic polymer. Any formulation suitable for application to the skin (e.g., a liquid, which can be applied as a spray, or a powder) can be used to form the "nanodrape" described below. In another embodiment, the formulation is provided as a coating on a device, for example a stent or a catheter, which may be dissolved in an aqueous solution and dried on the device, or mixed with a polymeric carrier and applied to the device. In yet another embodiment, the formulation is provided in a bandage, foam or matrix, in which the peptides may be dispersed or absorbed. The formulation could also be in the form of sutures, tape, or adhesive.

Conventionally, local anesthetics are delivered by topical administration (e.g., formulated as an ointment, cream, or solution) or injected into an area where the nerve fibers one wishes to block reside. The formulation may be administered to a burn or ulcer, especially when formulated with anesthetics, anti-inflammatories, growth factors, and anti-infectives, in the form of a foam, matrix or bandage, to stop bleeding or loss of interstitial fluid.

One or more of the compositions described herein can be assembled in kits, together with instructions for use. For example, the kits can include a biocompatible composition including self-assembling peptides (or a concentrated solution or powdered formulation thereof, together with a diluent) and a vasoconstrictor, a coloring agent, or an analgesic or anesthetic agent and instructions for their combination (if not already combined) and use (e.g., dilution and administration). The kits can further include one or more of the additional agents described herein. These agents can be present within a peptide-based composition or packaged separately, and they can include one or more types of biological cells, an antibiotic or other therapeutic, collagen, an anti-inflammatory agent, a growth factor, or a nutrient. The kit may also include one or more of a syringe (e.g., a barrel syringe or a bulb syringe), a needle, a pipette, gauze, sponges, cotton or the like, swabs, a bandage, a nosebleed plug, a disinfectant, surgical thread, scissors, a scalpel, a sterile fluid, a spray canister, including those in which a liquid solution is sprayed through a simple hand pump, a sterile container, or disposable gloves.

The formulation can be administered as appropriate for treatment of one or more disorders. For example, the formulation may be applied to repair an injury or dealing surgery of the lung or dura, or following an epidural or spinal tap, to stop leakage of cerebrospinal fluid. The formulation may be dispersed in a suture or adhesive for administration at the time of or as released following suturing or gluing of a wound, thereby limiting bleeding, loss of tissue fluids, or other fluids such as those produced by parenchymal tissues such as the liver, pancreas, and gastrointestinal tract. The formulation may be applied to any site of bleeding, in a bandage, gauze, sponge, or other material, for immediate control of bleeding, or released later to control bleeding if the initial treatment such as suturing or pressure is insufficient. Dried fabric, dehydrated foams or hydrogels, or bandages containing the formulation may be part of first aid kids for treatment of injuries, for example, in war, at accident sites, or clinics where rapid treatment may be required and storage space is limited.

In some embodiments, compositions including self-assembling agents can be associated with surgical sponges. For example, liquid compositions can be drawn into commercially available sponges prior to or during their use. Studies indicate that hemostasis can be satisfactorily achieved without traditional sponges, but there may be instances where including compositions containing a self-assembling agent may be beneficial (e.g., where a patient is experiencing profound bleeding or where the goal of treatment is temporary stabilization). The compositions employed can include any of the non-fibrous agents described herein. The sponges can be any known in the art, including woven and non-woven sponges and those designed specifically for dental or ophthalmic surgeries. See, e.g., U.S. Pat. Nos. 4,098,728; 4,211,227; 4,636,208; 5,180,375; and 6,711,879.

In embodiments featuring bandages or dressings, the bandage or dressing can include a first layer of sufficient shape and size to cover a wound or a substantial portion thereof (e.g., the most injured portion of the tissue or the area bleeding most profusely). The first layer can have a top surface, a bottom surface, and a perimeter that is, optionally, wholly or partially covered with an adhesive. A second layer of the bandage or dressing can be detachably affixed to the bottom surface of the first layer, optionally excluding the perimeter or any part of the perimeter bearing adhesive, and can include a liquid or non-liquid composition (e.g., a gel, paste, foam, cream, ointment, or powdered composition) including self-assembling peptides. The composition will come in contact with the wound upon application of the bandage or dressing and is transferable from the bandage or dressing to the wound site upon removal of the first layer or the first and second layers. In simpler configurations, the composition comprising self-assembling agents (e.g., peptides) can be associated with the bottom of the first layer (e.g., interior to the adhesive perimeter), and the second layer can be omitted. In either case, either the first and/or second layers can include a transparent window, through which some or all of the underlying wound can be viewed. The composition including the self-assembling agent(s) can be added to the bandage before it is packaged or just before use. In another embodiment, the formulation may include a further physical barrier, such as a layer of silicon film, to prevent loss of fluid by drying, after the active flow of fluids has been stopped by application of the formulation.

The formulations may also be administered as immediate or controlled release formulations. A delayed release dosage form is one that releases a drug (or drugs) at a time other than promptly after administration. An extended release dosage form is one that allows at least a twofold reduction in dosing frequency as compared to the drug presented as a conventional dosage form (e.g. as a solution or prompt drug-releasing, conventional solid dosage form). A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, matrix-forming compositions and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit™, (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants. Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet or wafer manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone™ XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer™ 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

Extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include methyl acrylate-methyl methacrylate, polyvinyl chloride, and polyethylene. Hydrophilic polymers include cellulosic polymers such as methyl and ethyl cellulose, hydroxyalkylcelluloses such as hydroxypropyl-cellulose, hydroxypropylmethylcellulose, sodium carboxymethylcellulose, and Carbopol™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers. In certain embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

An immediate release portion can be added to the extended release system by means of either applying an immediate release layer on top of the extended release core using a coating or compression process or in a multiple unit system such as a capsule containing extended and immediate release beads. Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils. Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies. The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Polymeric Matrices

Both non-biodegradable and biodegradable matrices can be used for delivery of the self-assembling peptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provided more effective results. The polymer may be in the form of a hydrogel (typically in absorbing up to about 90% by weight of water), and can optionally be crosslinked with multivalent ions or polymers.

Representative synthetic polymers that can be used for delivery include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene and polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lacetic acid and glycolic acid, polyanhydrides, poly(ortho) esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The polymer can also be in the form of a coating or part of a stent or catheter, vascular graft, or other prosthetic device.

The matrices can be formed by solvent evaporation, spray drying, solvent extraction and other methods known to those skilled in the art.

Bioerodible microspheres can be prepared using any of the methods developed for making microspheres for drug delivery, for example, as described by Mathiowitz and Langer, *J. Controlled Release* 5:3-22 (1987); Mathiowitz et al., *Reactive Polymers* 6:275-283 (1987); and Mathiowitz et al., *J. Appl. Polymer Sci.* 35:755-774 (1988). The selection of the method depends on the polymer selection, the size, external morphology, and crystallinity that is desired, as described, for example, by Mathiowitz et al., *Scanning Microscopy* 4:329-340 (1990); Mathiowitz et al., *J. Appl. Polymer Sci.* 45:125-134 (1992); and Benita et al., *J. Pharm. Sci.* 73:1721-1724 (1984). In solvent evaporation, described, for example, in Mathiowitz et al., (1990), Benita et al. (1984), and U.S. Pat. No. 4,272,398 to Jaffe, the polymer is dissolved in a volatile organic solvent. The peptide either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. In general, the polymer can be dissolved in methylene chloride. Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of peptides. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000. Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used. In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib et al., *Pharmazeutische Industrie* 40-11A, 1230 (1978). Chitosan microspheres can be prepared by dissolving the polymer in acidic solution and crosslinking with tripolyphosphate. For example, carboxymethylcellulose (CMC) microspheres can be prepared by dissolving the polymer in an acid solution and precipitating the microspheres with lead ions. Alginate/polyethylene imide (PEI) can be prepared to reduce the amount of carboxyl groups on the alginate microcapsules.

Other delivery systems including films, coatings, pellets, slabs, and devices can be fabricated using solvent or melt casting, and extrusion, as well as standard methods for making composites. The polymer can be produced by first mixing monomers and PEPTIDES as described by Sawhney et al., and polymerizing the monomers with UV light. The polymerization can be carried out in vitro as well as in vivo.

D. Devices for Administration

The liquid formulations may be provided in a syringe or pipette having a barrel containing a composition including self-assembling peptides and a means for expelling the composition from an open tip of the syringe or pipette (e.g., a plunger or bulb). The syringe may consist of one or more compartments (e.g., created by a divider running symmetrically or non-symmetrically along a long axis of the syringe barrel), so that mixing of the self-assembling peptides with one or more other agents occurs at the time of application. The compartments may also contain excipient such as a material forming a hydrogel or adhesive in a first compartment and the self-assembling peptides in a second compartment. In another embodiment, a first compartment may contain lyophilized self-assembling peptides or particles of self-assembling peptides, and a second compartment may contain a solution to dissolve or hydrate the peptides or powders for dry application. The composition within the barrel can further include any of the non-fibrous agents described herein (e.g., one or more of a vasoconstrictor, a coloring agent, an anesthetic or analgesic agent, an antimicrobial (e.g., antibiotic, antiviral, or antifungal agent) or other therapeutic, collagen, an anti-inflammatory agent, a growth factor, or a nutrient). In yet another embodiment, the material can be gelled and applied with an instrument, such as a spatula.

II. Methods of Administration

Any of the agents described herein, including cells, therapeutic, prophylacetic or diagnostic compounds such as antibiotics and growth factors can be introduced into the peptide solution prior to self-assembly in vitro or in vivo, and premolded structures can include one or more of these agents, optionally packaged in sterile material and/or provided with instructions for use. The material can be used prophylactically or as a treatment in the absence of additional agents. The bioactive agents can be approximately evenly distributed throughout the scaffold or concentrated in one area or another (e.g., on or near the surface, within a core area, graded throughout the scaffold or a region thereof, or layered therein (e.g., concentrated in layers or evenly or unevenly distributed)). To achieve an approximately even distribution of the substance within the structure, one can mix the precursor-containing solution and the substance, which may also be in solution, prior to initiation of self-assembly.

A. Sites of Administration

The material can be applied to a variety of different surfaces to prevent or control fluid passage (e.g., to promote hemostasis) or to function as a barrier (e.g., to reduce contamination). The amount of self-assembling agent is determined in part by the function of the material in controlling fluid flow, as well as the properties of any other materials or structures associated with the self-assembling peptides, alone or in combination with other bioactive materials.

In a first embodiment, the material is used to prevent or control bleeding. The material may be applied as a liquid, a gel, or as part of a substrate such as a bandage or membrane. Thus, formulations may be applied to a blood vessel, either within the lumen, for example at the time of angioplasty, administered by or as a coating on a stent or catheter, or exterior to the vessel, typically at the site of anastomosis. The material may be applied to tissues before, during or after surgery, to prevent bleeding, which is especially problematic with tissue such as liver, kidney or spleen, or other surgeries where there is a high risk that transfusion will be indicated, or to seal and protect a tissue (for example, a tissue selected or harvested for transplantation or a tissue suitable for reattachment (e.g., a severed digit)).

The material is also particularly well suited to use in the eye to prevent hemorrhage or bleeding within the vitreous humor (i.e., to promote hemostasis). Other surgeries where the material should be beneficial include corneal transplants, conjunctival surgery and glaucoma surgery. The material is particularly advantageous during surgery since it is clear and the surgeon is able to see through the material as he or she operates.

The material can be used to stop or impede the flow of fluids other than blood. The material can be applied to burns to stop or impede leakage of interstitial fluid. The material can be applied to the dura or lung as a dural or lung sealant.

The material can also be utilized in general oral surgery, periodontistry, and general dentistry, both as a barrier and to control or prevent bleeding.

The use of the material in individuals with impaired coagulation (hemophilia, von Willebrands, vitamin K, protein S or protein C deficiency, fulminant hepatitis, disseminated intravascular coagulation ("DIC"), hemolytic-uremic syndrome ("HUS")) is also an important utility since the mechanism of action is independent of the normal coagulation pathway.

In another embodiment, the material is applied to the exterior of a tissue such as a tumor, to prevent breakage or metastasis at the time of surgery. One of the benefits of the material is that it can be injected and gel in place, so that the material can be applied and reapplied during surgery, as necessary.

In still another embodiment, the material is particularly well suited to functioning as a barrier to prevent or reduce contamination, either to the tissue or from one tissue to another, for example, during intestinal surgery. The material may be applied to prepare an internal site prior to or during surgery, especially sites such as the sinus cavities, and for surgeries such as transurethral and transvaginal surgery, and as a prophylacetic and/or therapeutic. The material should also be particularly useful in cardiovascular surgery, where both barrier and hemostasis properties can be of value, for example, for heart valve patients who are prone to adverse consequences such as valve ring abscesses (coat valve, add antibiotic), endocarditis (coat valve), aortic root dissection (provide immediate hemostasis).

The material in combination with a metal such as silver has anti-adhesive properties and can inhibit angiogenesis. Accordingly, it may be useful in decreasing scarring and adhesions, including those that tend to occur following a surgical procedure. The material can be applied after surgery, or to an injury such as a burn, to decrease scarring and/or fluid loss, and to limit infection or the risk of infection. This has further application in plastic surgery, especially for protection of areas cleaned and debrided prior to closure or skin transplant, for example, in abdominoplasty, face lifts, flap donor sites, latissimus dorsi for breast reconstruction.

In still another embodiment, the material is administered as a slurry that can be drunk by a patient to reduce stomach bleeding, for example, from an ulcer, or to decrease acidity, or to limit bleeding from esophageal varices. Alternatively, the material can be provided as an enema to treat hemorrhoids or to fill in diverticula.

In yet another embodiment, the material can be used for a fertility treatment, preservation of eggs, and repair of scarred fallopian tubes.

The material may also be used as a blood stabilizer or as an organ preservation material.

As assembly is not irreversible, contained substances can be released. For example, the molecules or cells can be released from the structures in vivo (e.g., small molecules can diffuse away and larger molecules and cells can be released as the structures degrade).

In still another embodiment, the material, including formulations that contain non-fibrous and/or therapeutic agents or cells, is used as a neuroprotective to minimize damage and scarring following neural injury. Peptide-based structures promote repair and regeneration of neural tissue (e.g., when self-assembling peptides are applied to a lesion in the brain as described in U.S. Ser. No. 10/968,790). The small size of the fibers within the scaffolds and/or the open "weave" structure of the materials permits extension of cell processes and allows adequate diffusion of nutrients and waste products in a manner that provides unique advantages for neural tissue regeneration.

Peptide-based structures, including those that contain non-fibrous and/or therapeutic agents or cells, are able to enhance repair of non-neural tissues (e.g., epithelial tissues such as skin) when applied to an area of damage (see Example 5). Accordingly, the compositions can be applied outside of the central nervous system; outside of the brain; or to tissues outside the cranial cavity or spinal cord or column. The repair may constitute an anatomical or functional restoration of the tissue to a condition resembling that of the tissue prior to the injury or deterioration (e.g., disease-associated deterioration). The repair should be superior to that which one would expect in the absence of treatment with a present composition. For example, the repair may include restoration of physical continuity between two portions of a tissue that were separated by injury, deterioration, or other damage. Preferably, the restored physical connection will include reapposition or reconnection of the portions of tissue without appreciable separation by heterogeneous tissue, such as scar tissue.

In the course of promoting wound repair, the compositions may not only improve the final outcome (e.g., reduced scar formation resulting in an outcome that more closely resembles the original tissue), but also reduce the time required for healing. These results could not have been predicted on the basis of the results achieved following application to the injured central nervous system, given the substantial differences between neural and non-neural tissues.

B. Effective Dosages

In general, the amount of material required will vary depending on various factors such as the size or extent of an injury (which can, in turn, be expressed in terms of the length of an incision, the caliber or number of damaged blood vessels, the degree of a burn, the size and depth of an ulcer, abrasion, or other injury). The amount may vary, for example, from a few microliters to several milliliters or more, e.g., tens or hundreds of milliliters. The device used to deliver the material will vary in accordance with the amount. For example, a syringe can be conveniently used to deliver smaller amounts, whereas a tube or squeezable bottle would be more suitable for larger amounts. An effective amount (whether in reference to a scaffold, precursors thereof, or another bioactive molecule present in the formulation), means the amount necessary to elicit an improved or desired biological response.

As will be appreciated by those of ordinary skill in this art, the effective amount of an agent may vary depending on such factors as the desired biological endpoint, the agent to be delivered, the nature of the site to which the agent is delivered, and the nature of the condition for which the agent is administered. For example, an effective amount of a composition for accelerating hemostasis may be an amount sufficient to decrease the amount of blood lost between the time that bleeding begins and the time when bleeding ends by at least 25% relative to the amount of blood lost following treatment with cold saline or no treatment. An effective amount of a composition for accelerating hemostasis may also be an amount sufficient to decrease the time required to achieve cessation of visible bleeding by at least 25% relative to the time required following treatment with cold saline or no treatment. An effective amount of a composition for promoting wound healing may be an amount sufficient to decrease the time required to achieve a predetermined percent reduction in the size of a lesion by at least 25% relative to the time required in the absence of such treatment.

The amount of the composition provided can vary depending on the severity of the subject's condition and should be sufficient to inhibit the unwanted movement to an extent that benefits the subject. The bodily substance can be blood, cerebrospinal fluid, pus, serous exudate, bile, pancreatic juice, or a substance normally contained within the gastrointestinal tract (e.g., the stomach or intestine), or urinary tract.

C. How Administered

The composition can be provided on the surface of the subject's body and/or provided within a cavity generated by force (e.g., by unexpected trauma or a surgical procedure). In this way the unwanted movement of a bodily substances can be inhibited in the context of a wide range of situations, including traumatic injury, a medical condition (e.g., a chronic or prolonged medical condition associated with bleeding), or surgical procedures (e.g., orthopedic surgery, dental surgery, cardiac surgery, ophthalmic surgery, or plastic or reconstructive surgery). For example, where the unwanted movement of the bodily substance is the result of trauma, the subject may have a partly or completely severed body part, a laceration, abrasion, puncture wound, or a burn. Where the compositions are applied to a surface of the body, they may not only inhibit the unwanted movement of a bodily substance, but also help protect the subject from contamination. For example, applying a self-assembling agent to the skin will impede the movement of an unwanted foreign substance on the skin or hair into a wound. When the unwanted movement of the bodily substance results from a chronic medical condition, the subject may experience recurrent bleeding. For example, the subject may be experiencing bleeding in connection with varicose veins, including telangiectases, hemorrhoids, bleeding in the lungs (due, for example, to lung cancer, bronchitis, or a bacterial or viral disease, including pneumonia or influenza), or esophageal varices. Medical conditions associated with recurrent bleeding can be treated with the compositions described herein, including those that contain self-assembling peptides and a vasoconstrictor (e.g., phenylephrine, which can constitute about 0.25-0.5% of the composition). Where bleeding occurs in the oropharnyx or lungs, the compositions can be administered through a metered dose inhaler. If the patient's condition has deteriorated to the point where artificial ventilation is required, the compositions may be administered through a respirator or by lavage.

The unwanted movement of the bodily substance can also take place during a surgical procedure, and that procedure can involve an incision within the subject's nervous system, eye, ear, nose, mouth, pharynx, respiratory system, cardiovascular system, digestive system, urinary system, reproductive system, musculoskeletal system, liver, or integument. The methods can be carried out regardless of whether or not the movement of the bodily substance was intentional. The compositions described herein can be applied before or after the unwanted movement occurs (e.g., during a surgical procedure before the intentional transection of a blood vessel or after an unintentional transection of a blood vessel). For example, the surgical procedure can be carried out with the intent to repair an aneurysm, impede bleeding within the brain, to treat esophageal varices, to treat an ulcer or to inhibit the loss of gastric contents or intestinal contents (e.g., from a swollen or ruptured appendix). The surgical procedure can involve resecting a portion of the subject's intestine. Other procedures that can be carried out with the assistance of compositions including self-assembling agents include arteriography, cardiac catheterization, insertion of a stent, assistance with a natural birth or birth by Caesarean section, hysterectomy, organ transplant, joint replacement, or excision of (or other manipulation of) an intervertebral disk. These procedures are representative. The surgical procedure can be performed with the assistance of an endoscope or laparoscope, and the compositions can be delivered independently or from a chamber situated within these devices and connected to a distal end by a passage for release onto the subject's tissues. Where the patient has an ulcer, that ulcer can be an esophageal, gastric, duodenal, diabetic, or decubitus ulcer. More generally, the compositions can be applied to any disrupted area of the skin, and any of the methods described herein can include a step of identifying a patient in need of treatment.

A self-assembling peptide nanofiber scaffold (SAPNS) can provide a transparent environment for the surgical field, while also creating an optically clear liquid that allows operation through the resultant liquid and gel mix. The surgical field is often obscured with blood and debris during an operation. In addition, clearing debris from the surgical field usually requires irrigating the site with saline. Saline is only a temporary solution and needs to be continuously applied to maintain a clear surgical field. This poses several issues: any contamination in existence will easily spread; a small opening will require alternating between irrigation and operating; and during intestinal operations use of saline can result in a massive infection leading to post-operative complications. Using the SAPNS for biological confinement will reduce post operative complications in endoscopic and open surgical procedures. Efficacy has been demonstrated on brain, spinal cord, gastrointestinal tract, liver, muscle, arteries and veins. For example, a partial resection is currently performed as follows. The surgeon performs a partial resection of the intestine to remove a precancerous area. The incision is made and the intestines are gently lifted out of the intraperitoneal cavity and placed on the table next to the patient. The offending area is resected and the two ends of the intestine are then ligated together. Before the intestines are put back in the body there is a colostomy bag connected to the upper end of the intestine and the area of the operation is disinfected. The intestines are replaced in the abdomen and are sewn back up. A drain is placed in the abdomen to make sure there is no leakage or bleeding. In contrast, using the self-assembling peptide material, a partial resection is performed as follows. The doctor opens the abdomen and finds the offending part of the intestine. It is isolated with additional liquid that is poured into the intraperitoneal cavity to isolate it from the rest of intraperitoneal cavity. The surgeon reaches through the gel that was formed by the liquid and resects the intestine. The two ends are ligated together and the area is checked for any changes in color (the gel may also have an indicator die that changes color (e.g., to blue) if there is any leakage of gastric fluids or bacteria). The colored material is removed (e.g., with suction). A little more material can be sprayed around the area of the repair before the abdomen is sewn up. In summary, the self-assembling peptide material can be used to create a cleaner local environment to perform surgery; isolate structures and impede migration of contaminates; inflate structures for surgical procedures (e.g., intestine); surround structures that are being removed that may leak (e.g., appendix); patch holes in a body; allow for a better surgical outcome in dirty environments; facilitate scope procedures to surround the organ before the operation to contain any leakage; create a barrier to prevent or impede adhesions while performing abdominal surgery; and used to form a gasket between the scope and the insertion point of the scope. Benefits may include one or more of the following: the material is optically clear, has a long shelf life at room temperature, can be operated through, shortens prep time, eliminates counting sponges, isolates each structure in the surgical field, shortens clean up time of the operating room, shortens surgical time, reduces or eliminates cross contamination caused by other irrigants. Further, the material is biocompatible, and the breakdown products can be natural and can be absorbed by the body. The material is also easy to manipulate, can be injected at the location needed, reduce Staphylococcal infections or the risk of infection, may be able to reduce the cost of surgical theater disposables such as paper, and may reduce biohazard bags since the material can be boiled to sterilize after the procedure to yield steam. Since the material is clear it should enable the surgeon to operate faster because the operating field is clear of blood. The elimination of wound packing to control bleeding could reduce the operating time as much as 50% in a complicated case. Post-operative infection, due to secondary infection, may be reduced by the use of the material since it can coat the wound during and after surgery, thus reducing contamination from foreign bodies. In post-operative care, one can use the material to reduce infection due to undesirable drainage by slowing the spread of particulate material within the abdomen or chest cavity.

While the compositions can be removed from a site of application (e.g., a bleeding vessel) at any time, a physician may wish to allow them to remain in place even after the initial goal of promoting hemostasis has been achieved (e.g., in order to promote wound healing).

Where the compositions include self-assembling peptides, those peptides can include amino acid residues that are naturally occurring and that can be absorbed by the body. as noted, the compositions are not difficult to manipulate, and they can be easily dispensed on an as-needed basis. Their features (e.g., stiffness) can be altered readily by altering the concentrations of components therein (e.g., by altering the concentration of self-assembling peptides in a given composition). As the resulting, assembled structure does not significantly impair one's view of an underlying tissue, and does not have to be removed before or after a procedure is carried out, one can assess a wound through the material. For example, a physician can assess a burn or other surface trauma that has been treated in the field with a composition described herein. In the operating room, a surgeon can make an initial incision through the material and can continue to operate with standard equipment, such as scalpels and clamps, or more modern means, such as lasers, in an internal field to which the compositions may also have been applied. As the compositions can be applied around the site of an incision and form a coating to protect against infectious agents, there is less need to shave a patient's skin, apply drapes, and apply disinfectants.

Given the structural integrity of the assembled scaffolds, they can be removed from an area in which they have formed if desired. Thus, an assembled scaffold can be removed by, for example, suction, or by lifting it away with an instrument such as forceps, or wiping it away with a swab or gauze. For example, the scaffold can be removed after hemostasis is achieved or in the course of cleaning a wound. Based on studies to date, the scaffold or a majority thereof can be removed without damaging the underlying tissue. Where the assembled scaffolds are formed ex vivo, they can be removed from a mold and used subsequently (e.g., implanted in a tissue or tissue void). The compositions should reduce the amount of material that requires disposal or cleaning afterward (e.g., surgical drapes, sponges, and other biohazards). "Nanodrapes" can be used to replace traditional paper or cloth drapes, by limiting infection following application directly to the patient, for example, by spraying or otherwise coating the patient or the area around the surgical incision. Currently a patient is prepared for surgery by shaving, scrubbing, disinfecting and draping after positioning on the surgical table. Then bactericide and tape is applied to the area where the surgery is to be performed. A self-assembling composition can be applied in place of drapes by spraying a liquid formulation (which may be warmed) onto the body where it self-assembles into a thin coating (or "second skin"). Preferably, the material will have a pore size (or average pore size) that is smaller than any bacteria (e.g., a *Staphylococcus aureus*). The pore size will impede contaminants, including airborne contaminants, from reaching the patient's skin or a wound. The coating or second skin can be at least or about one millimeter thick, and the material can contain an antimicrobial agent (e.g., a mild anti-bactericide). whenever applied to the skin, the material can also include a hydrating component for the skin so it does not dry out.

A scaffold (e.g., a nanoscale structured material) can be provided by introducing, to a subject (e.g., a human patient), a precursor of the scaffold at a location, or in the vicinity of a location, where the scaffold is desired (e.g., to control movement or leakage of a bodily substance, to protect a wound, or to promote tissue repair). Precursors (e.g., self-assembling peptides) are provided in the vicinity of a location when they are provided at a position that is close enough to the targeted area (e.g., a bleeding vessel, a diseased section of the digestive tract, or an area of burned skin) that they reach the targeted area in an effective amount. The precursors, which may be homogenous or heterogeneous (e.g., one may apply a single type of self-assembling peptide or a mixture of two or more different such peptides), can be contained within a composition and, upon contact with physiological conditions, assemble to form the scaffold (e.g., a nanoscale structured material). Thus, the precursors can assemble in situ (i.e., within the body of a subject at or in the vicinity of administration).

The nanoscale structured material may include, or its assembly may involve, additional components present in situ (e.g., ions). Thus, precursors such as self-assembling peptides can be applied in a solution that is substantially free of ions (e.g., substantially free of monovalent cations) and self-assemble to form a macroscopic structure when they come in contact with such ions in the body (e.g., in a bodily substance such as blood, gastrointestinal contents, and the like). For example, a solution containing precursors can be applied at, or in the vicinity of, a site of gastric or intestinal perforation or a site where a surgical incision has been or will be made.

The scaffold can also be provided in the form of a gel, as the precursors (e.g., self-assembling peptides) can be assembled prior to introducing a composition to a targeted area (e.g., the site at which an incision will be made for a surgical procedure). The assembled structure may assume any convenient shape.

The scaffold can also be provided by providing precursors in the form of a dry powder. A "dry" powder will have a relatively low liquid content (e.g., sufficiently low that the particles therein are readily dispersible). Self-assembling peptides provided in the form of a dry powder will assemble when they come into contact with a bodily fluid containing monovalent cations, and a solution containing such ions may be added if desired to alter the rate at which the scaffold forms or its stiffness. Self-assembling peptides may be provided as emulsions or, as described above, molded into preformed shapes that can be inserted into a body cavity or wound site in a manner similar to the manner that surgical sponges are currently used. If desired, a binder can be added to a dry powder which is then formed into a desired shape. Regardless of the precise manner in which the scaffold is assembled (e.g., whether by bringing a liquid formulation containing precursors into contact with the body or a dry powder into contact with an ion-containing solution ex vivo), the formed scaffolds can assume a desired shape. Where the size and shape is such that the scaffold fills the lumen of a blood vessel, the scaffold can be used a vascular plug.

A preventative measure can be carried out before a subject experiences an unwanted event (e.g., before an injury occurs or before bleeding begins). Thus, the site of administration can be a site of potential movement or potential leakage, and the application can be made to prevent or minimize such movement or leakage should it occur. When used in the context of a therapeutic procedure or treatment, the compositions can reverse, alleviate, or inhibit the progress of a condition (e.g., a state, syndrome, disease, or a sign, symptom, or manifestation of such). Methods of treating a subject are generally carried out once the subject is recognized as having a condition amenable to treatment, and any of the methods described herein, whether best described as prophylacetic or therapeutic, can include a step of identifying an amenable subject (e.g., a subject considered in need of the treatment or procedure prescribed and subsequently carried out (e.g., a patient who is bleeding or scheduled to undergo a surgical procedures)).

As the compositions described here can be used to inhibit movement of a bodily substance in a subject, including movement within or from the epidermis, the compositions can be employed in the context of performing surgery and may be described as new methods for performing surgery or generating a surgical field. The methods, whether performed in the context of surgery or not, can include a step of identifying a subject in need of treatment and a step of providing a nanoscale structured material, or a precursor thereof, at or in the vicinity of a site where unwanted movement has occurred or is expected to occur. The amount of the composition administered and the concentration of self-assembling peptides therein can be sufficient to inhibit the unwanted movement of a bodily substance. For example, one can identify a patient who is about to undergo a surgical procedure and provide a biocompatible composition comprising self-assembling peptides and a vasoconstrictor, a coloring agent, or a local anesthetic agent to a site at which an incision or other invasive maneuver will be made or has been made. The bodily substance that is affected may be a fluid such as blood or a blood product, serous exudate (an inflammation-associated exudate composed largely of plasma, which typically appears as a clear or amber-colored fluid), pus, gastric juice, urine, bile, cerebrospinal fluid (CSF), pancreatic juice, and the like. The bodily substance may be viscous, sludge-like or semi-solid but will generally exhibit an ability to flow or move. Substances of this nature include the contents of the gastrointestinal tract. The composition may be removed after application (e.g., after hemostasis is achieved or an operation on the bowel is complete) or may be left in place. For example, the compositions can be applied to accelerate hemostasis or inhibit movement of intestinal contents during surgery and some or all of the scaffold may be left in place when the operation is complete. This provides a substantial advantage relative to the use of sponges and other materials that must be removed prior to closure. The compositions can be removed in a variety of ways (e.g., by wiping or by suction).

The compositions can also be applied to shield an underlying area (e.g., an area of burned or otherwise injured skin or other tissue) and can, therefore, help to prevent contaminants (e.g., foreign substances) from coming into contact with the area (i.e., the compositions can be used as a barrier or shield). A physician or other health-care provider can examine a wound through the material, and a surgeon can operate through it, while it is in place. Contaminating substances that have landed on the material during the procedure could then be removed by virtue of removing the material.

The compositions can be administered to stabilize a wound prior to definitive treatment (e.g., while the victim is awaiting transport to a hospital or during transmit). The compositions are similarly useful where operations are conducted under conditions of less than optimal sterility (e.g., in field hospitals or in areas of the world where access to sterile operating rooms is limited). The compositions and methods have the potential to significantly reduce the likelihood of contamination in instances such as these.

The self-assembling peptide material can also be locally applied in combination with anesthetic in the local area where a procedure is to take place and can be applied at a higher concentration to reduce organ movement during surgery. This may reduce cognitive deficits to older patients by reducing the general anesthetic load. A thin layer can be sprayed on the tissue or skin where the surgeon is operating. It can be applied separately or together, administering specific anesthetic for specific organs. Skin has different receptors than intestines and the need for a specific anesthetic is needed for each of the organs. Intestines need to stop moving during surgery while the blood and blood vessel contraction need to remain constant.

Treatment and prevention of bleeding: Any individual who has an increased risk of suffering undesirable bleeding, which may or may not be excessive or immediately life-threatening, can be treated with the compositions described herein. These individuals include those with blood clotting disorders such as hemophilia, patients who are receiving anticoagulant therapy, patients who suffer recurrent nosebleeds, and individuals undergoing surgery, particularly major surgery or procedures that involve accessing an artery. Without limitation, the surgery or procedure can be an operation on the nervous system, eye, ear, nose, mouth, pharynx, respiratory system, cardiovascular system, digestive system, urinary system, musculoskeletal system, integumentary (skin) system, or reproductive system. As noted, the compositions can also be applied to tissues exclusive of those that define the central nervous system (i.e., the brain and spinal cord). Specific examples of surgeries and procedures in which the compositions can be used include arteriography, angiocardiography, cardiac catheterization, repair of obstetric laceration, removal of coronary artery obstruction, insertion of stent, Caesarean section, hysterectomy, reduction of fracture, coronary artery bypass graft, cholecystectomy, organ transplant, total joint (e.g., knee, hip, ankle, shoulder) replacement, appendectomy, excision or destruction of intervertebral disk, partial excision of the large intestine, mastectomy, or prostatectomy. The surgical procedure can involve the intentional or unintentional transection of a blood vessel or causing the release of a bodily substance other than blood.

Accident victims, individuals engaged in combat, and women giving birth are also at risk of experiencing significant blood loss. The compositions can be applied to a site of obstetric bleeding (e.g., within the uterus, vagina, or neighboring tissue) in order to accelerate hemostasis. For example, the compositions can be applied to a placental tear or used to pack the uterus to control bleeding. As with other indications, compositions applied to the reproductive tract can be removed or left in place. Spontaneous hemorrhage, aneurysm rupture, esophageal varices, gastric ulcers, ulcers of the upper portion of the intestine (e.g., duodenal ulcers) are also medical conditions in which considerable bleeding can occur, and these individuals can also be treated as described here.

The precise source of the bleeding can vary and can be from any blood vessel in the arterial or venous system (e.g., an artery, arteriole, capillary or capillary bed, venule, or vein). The size of the vessel may range from large (e.g., the compositions can inhibit bleeding from the aorta, the iliac or femoral artery, or a portal vein) to small (e.g., a capillary), and the vessel may be located anywhere in the body (e.g., in a solid organ such as liver, the stomach, intestine, skin, muscle, bone, the lungs, or the reproductive system).

The time normally required for blood clotting can be prolonged when plasma levels of clotting factors and/or platelets are low or in cases in which an individual has received an anticoagulant (e.g., warfarin or heparin). Bleeding frequently persists for considerably longer than the average clotting time when there is more than minimal damage to blood vessel integrity. Based on the studies, it is expected that the compositions will cause hemostasis in a period of time that is less than, and in at least some cases much less than, the average blood clotting time. Although the compositions are not limited to those that achieve hemostasis in any given time (and uses such as protecting an area from contamination or promoting tissue healing are independent of this function), the compositions may confer a benefit to a bleeding subject in as little as five seconds following application. Other compositions can exert an effect in about 10, 15, or 20 seconds following application. The effective period can be characterized in a manner other than absolute time. For example, compositions may reduce the time required to achieve hemostasis by between 25% and 50%; between 50% and 75%; or between 75% and 100% relative to the time required when iced saline is applied. The time required to achieve hemostasis can be reduced by approximately 2-, 3-, 4-, or 5-fold relative to the time required when iced saline is applied.

The peptide concentration may be selected with reference to variables such as the caliber of the vessel, the extent to which it has been injured, and the force with which blood is exiting (or would exit upon injury). Higher peptide concentrations will be desirable to promote hemostasis from a major vessel (e.g., the aorta, brachiocephalic, carotid, subclavian, celiac, superior mesenteric, renal, iliac, femoral, or popliteal arteries). Useful concentrations can range from between approximately 0.1-10% (e.g., 1-10%; 0.5-5%; 1-4%; 0.1-2%; 0.1-3%; 0.1-4%; 0.1-5%; and 1-8% (e.g., about 1, 1.5, 2, 2.5, 3, 4, 5, 6, or 7%). Any subrange, or any specific value within any of the aforesaid ranges, can be used. Any of the aforementioned concentrations may also be used for the other indications described herein.

As noted, bleeding can be due to any of a large number of different causes and can be internal or external. The compositions can be applied regardless of the cause or the nature of the cause (e.g. whether caused by a disease process or intentional or accidental trauma). The compositions can be used to achieve hemostasis in a confined space (e.g., inside a hollow organ) or at or near the body's surface. For example, the compositions can be applied to a partly or completely severed body part such as a limb or digit. In that event, the compositions may be serving multiple functions; they may not only promote hemostasis, but also protect the wounded tissue from contaminants and promote tissue healing. More specifically, the compositions can be applied to a wound, left in place for a period of time sufficient to achieve hemostasis and for blood clotting to occur, and then removed. Contaminating material such as particulates and infectious agents adhered to the peptide gel would be removed with it. A sterile dressing may then be applied. Of course the compositions can be applied for purposes of cleaning a wound, preventing contamination, or promoting tissue healing even after hemostasis has been achieved or in situations in which acceleration of hemostasis is not needed.

When used to treat a nosebleed, the compositions are inserted into the appropriate nostril and can be left in place until the bleeding has subsided. The compositions can be easily removed by suction (e.g., using an eyedropper or syringe) or may be removed by other physical means, including simply blowing the nose. If desired, the compositions can be administered to the nose by way of inclusion on one or more surfaces of a nosebleed plug.

The compositions can also be left in place on a wound, and a dressing can be applied over the composition. Since the composition itself is easily removed, its presence under the dressing can help prevent the dressing from sticking to the damaged tissue. If desired, a bandage having a transparent portion may be used so the injured site can be viewed through the transparent portion of the bandage and the peptide structure below. This would allow a physician to monitor the progress of the healing without removing the dressing. Modified bandages are described further below and are within the scope of the present invention.

Many medical procedures involve vascular puncture, which can be followed by significant bleeding. A self-assembling peptide composition can be applied to the wall of a punctured vessel, e.g., during withdrawal of an instrument used to puncture the vessel. A vascular plug formed from self-assembling peptides provides an alternative to existing vascular plugs and devices such as those described in U.S. Pat. Nos. 5,192,302; 5,222,974; 5,645,565; and 6,663,655. The vascular plug can be formed in situ (e.g., at a site of vascular puncture), or can be preformed and applied to the site.

More generally, compositions comprising nanostructured materials or precursors thereof (e.g., self-assembling peptides) can be used for sealing any passage through tissue. The present methods therefore include methods of sealing a passage through tissue by applying a composition comprising a nanoscale structured material (e.g., self-assembling amphiphilic peptides) to one or both ends of the passage or to its interior. The tissue can be, for example, the wall of a blood vessel, the wall of an organ, subcutaneous tissue, or adipose tissue. Sealing the passage can result in hemostasis. The passage can also be a fistula (i.e., an abnormal connection between two organs or body structures or between an organ or structure and the external world). If desired, a surgeon can apply the compositions to the interior of a tubular structure such as the intestine or a blood vessel, resect and ligate the intestine or blood vessel in the gel, and evacuate the gel from the interior of the structure to restore continuity of the structure and allow reperfusion of the area with blood or other body substances.

For surgical applications, the wound or any part of the surgical field can be packed with a composition comprising self-assembling peptides. This approach can be used instead of wound packing as it is conventionally performed during surgery. As the compositions contain biocompatible and biodegradable material, they can be left in place, thereby avoiding the need for removal at the end of the procedure and avoiding the need for a subsequent operation for this purpose. Biodegradable materials can be broken down physically and/or chemically within cells or within the body of a subject (e.g., by hydrolysis under physiological conditions or by natural biological processes such as the action of enzymes present within cells or within the body) to form smaller chemical species which can be metabolized and, optionally, reused, and/or excreted or otherwise disposed of. Preferably, the biodegradable compounds are biocompatible.

Gastrointestinal bleeding, which can occur as a consequence of ulcers or angiodysplasia, is a relatively common and serious condition that can be fatal if left untreated. Bleeding esophageal varices, and bleeding gastric or duodenal ulcers can be particularly severe. A number of endoscopic therapeutic approaches have been developed to achieve hemostasis, such as the injection of sclerosing agents, the attachment of mechanical hemostatic devices, and contact electrocautery techniques. The compositions can be administered at, or in the vicinity of, an ulcer or a site of bleeding in the esophagus, stomach, small intestine, or large intestine. Bleeding in the distal portion of the large intestine, rectum, or anus (e.g. hemorrhoids) can also be treated in this manner.

Rupture of an aneurysm can represent a catastrophic event with rapidly fatal consequences. Ruptured aortic aneurysms can rapidly result in exsanguination despite prompt medical attention. Ruptured intracranial aneurysms frequently have devastating consequences. The compositions and methods of the invention can be used to treat bleeding from a ruptured aneurysm in an essentially similar manner to the way in which they are used to treat bleeding due to other causes (e.g., by application of self-assembling precursors or a preformed structure to the site of bleeding). Given the often severe consequences of aneurysm rupture, surgical repair is often attempted. The compositions can be applied in the context of any attempted repair (e.g., during open surgery or endovascular repair (e.g., with placement of a graft and/or stent)). More specifically, the present methods include treating an aneurysm by introducing a composition comprising a nanoscale structured material or precursor thereof (e.g., a composition comprising self-assembling peptides) into the aneurysm (e.g., into the aneurysm sac). Once any bleeding is under better control, the aneurysm may then be repaired using any suitable technique. Presence of the peptide structure within the aneurysm sac reduces the chance of leakage or rupture prior to or during these other procedures. The scaffold can be left in place.

Inhibiting movement or leakage of cerebrospinalfluid (CSF): The dura mater is the tough, outermost, fibrous membrane that covers the brain and spinal cord, and lines the inner surface of the skull. Leakage of CSF is a significant complication following injury, surgery, or other procedures in which the dura mater is penetrated, including inadvertent penetration in the course of administering an anesthetic to the epidural space. Such leakage can lead to serious sequelae, such as severe headaches, infection, and meningitis. The composition can inhibit movement or leakage of CSF in a subject in need thereof after application at, or in the vicinity of, a site of unwanted movement or leakage of CSF. The compositions can be applied over sutures following dura mater surgery to help prevent CSF from leaking out of the incision site.

The compositions can also be used to inhibit movement or leakage of fluid from the ear drum.

Inhibiting leakage of contents of the gastrointestinal tract: The compositions can inhibit the movement of gastrointestinal contents. For example, the structures can prevent leakage of gastrointestinal contents following gastric or intestinal perforation or during surgery (see Example 4). The structures can be used to isolate such bodily substances and prevent their spread within the peritoneal cavity, thereby minimizing contamination and the risk of subsequent chemical peritonitis and/or infection. Gastric contents, which contain digestive secretions of the stomach glands consisting chiefly of hydrochloric acid, mucin, and enzymes such as pepsin and lipase, can cause injury and/or infection if released into the peritoneal cavity. Release of intestinal contents into the peritoneal cavity represents a frequent event during surgery on the intestine and can also occur in cases of intestinal perforation or a ruptured appendix. The composition can be used to inhibit leakage of gastrointestinal contents into the peritoneal cavity. The site of movement can be a site of gastric or intestinal damage caused by a disease process or a surgical incision. The compositions can be applied to the exterior of any organ in the digestive system (e.g., the stomach, or small or large intestine) or can be injected or otherwise introduced into their interior. The compositions can be administered in the course of resecting a segment of the intestine. For example, one can fill a segment of intestine that extends from a first point to a second point with a present composition and resect a portion of the intestine that lies between the first and second points.

In a related method, one can use the compositions to remove intestinal contents that have been released into the peritoneal cavity. The method includes applying a liquid composition to the released intestinal contents, allowing the liquid composition to undergo a phase transition, and then removing the gel-like or semi-solid composition. These steps can be repeated once or more until the surgeon is satisfied with the amount of intestinal contents that have been removed from the peritoneal cavity.

One can similarly inhibit movement of the contents of other internal organs (e.g., organs in the biliary or urinary systems). For example, one can inhibit movement of bile, pancreatic juice (i.e., secretions of the exocrine portion of the pancreas that contain digestive enzymes), or urine and/or decontaminate or clean an area into which bile, pancreatic juice, or urine have been released by application and subsequent removal of the compositions to the site. The methods thus have broad application to surgeries for repairing or otherwise treating intestinal, biliary, and/or urinary system defects. As noted herein, the compositions can be applied to the skin or to an incision in the skin or the wounded tissue underneath to reduce the likelihood of contamination from a microbe such as a bacterium. The methods can be used to decontaminate the site to which they have been applied by removing the compositions at a subsequent time (e.g., upon the completion of a surgical procedure).

Wound healing: Studies also indicate that the compositions have the ability to enhance healing, particularly of an epithelial layer or muscle, and can therefore be administered to treat a site of tissue damage. For example, one can apply a composition including self-assembling peptides to the site of tissue damage. The compositions appear to both increase the rate of tissue repair and inhibit formation of scar tissue. The compositions can be used for either acute or chronic wound care. For example, they can be applied to skin wounded in any manner (e.g., lacerated or burned) and to lesions such as diabetic ulcers and pressure sores.

Delivery Methods, Devices, and Kits: A variety of devices can be used to introduce the compositions to a target area of the body. The devices can be simple, such as a syringe, and such devices can be provided together with the compositions in kits. The composition can be locally delivered at or near a target area in the body by injection (e.g., using a needle and syringe), or with a catheter, cannula, or by dispensing (e.g., pouring) from any suitably-sized vessel. The compositions can be delivered with the assistance of imaging guidance (e.g., stereotactic guidance) if necessary. Alternately, a material can be wetted with the composition and then used to apply a composition to an area of tissue.

For storage and shipping, self-assembling peptides can be dissolved in a suitable solvent (e.g., an aqueous medium such as sterile water, and stored for long periods of time prior to use). Peptide-containing solutions have been stored for up to two years without substantial loss of activity. If partial self-assembly occurs after a prolonged period of time, physical agitation (e.g., sonication) can be used to restore the material to a more liquid state prior to administration. Alternatively, the material can be applied as a gel. If desired, a small amount of ions (e.g., monovalent cations) can be added to a solution prior to application. This may speed the process of gel formation. Alternately, monovalent cations can be applied after the solution has been administered.

Kits containing syringes of various capacities or vessels with deformable sides (e.g., plastic vessels or plastic-sided vessels) that can be squeezed to force a liquid composition out of an orifice are provided. In one embodiment, the syringe or vessel contains multiple compartments, one containing monovalent ions, and the other self-assembling peptides, which are mixed at the time of administration, through a common needle. An endoscope can be used to deliver the compositions for treatment of a hollow organ (e.g., the esophagus, stomach, intestine, etc.) or body cavity (e.g., during minimally invasive surgery). Minimally invasive surgery refers to an approach to surgery whereby operations are performed with specialized instruments designed to be inserted through small incisions or natural body openings, often performed with endoscopic visualization. Examples include laparoscopic surgery, arthroscopic surgery, and endovascular surgery. An endoscope is typically a long, flexible tube-like device. In addition to allowing visualization of internal structures, many endoscopes have additional diagnostic (e.g. biopsy) and therapeutic capabilities (e.g. delivery of therapeutic agents) through special channels. Colonoscopes, sigmoidoscopes, bronchoscopes, cystoscopes, and laparoscopes, are variants of an endoscope having features making them particularly well suited for viewing certain organs, structures, or cavities. Any of these devices can be used to deliver the compositions. Kits may be packaged including an endoscope and a vessel containing a solution comprising self-assembling peptides. Suitable endoscopes are known in the art and are widely available. Endoscopes are currently in use to deliver sclerosing agents to sites of esophageal bleeding.

Kits can include self-assembling peptides and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. The peptides can be in solution or dry (e.g., as a dry powder). Components of the kit may be packaged individually and are sterile. The kits are generally provided in a container, e.g., a plastic, cardboard, or metal container suitable for commercial sale. The kit may be styled as a "first aid kit," in which case it will typically have a symbol such as a red cross on the exterior. Any of the kits can include instructions for use.

EXAMPLES

Example 1

Self-Assembling Peptide Material Accelerates Hemostasis in the Brain

Complete transection of a branch of the superior sagittal sinus in the brains of rats and hamsters was performed after removing a portion of the skull overlying the transected tissue. Animals were anesthetized with an i.p. injection of ketamine (80 mg/kg) and xylazine (8 mg/kg). All surgical procedures were conducted under an operating microscope. Twenty-two animals, including 10 adult hamsters and 12 young adult female Sprague-Dawley rats (200-250 g), were treated with either iced saline or 20 µl of a 1% peptide solution at the site of the sinus branch transection. The material was prepared by dissolving RADA16-I (n-RADARADARADARADA-c; SEQ ID NO: 1) peptide in sterile water, and the peptide-containing solution was applied to the injured tissue with a 31 gauge needle attached to a 2 cc syringe.

The experiment was videotaped with a time stamp and was replayed one frame at a time to evaluate the length of time required for the peptide solution to form a gel, which effectively impeded bleeding. Hemostasis was assessed visually, and "complete hemostasis" was defined as the complete lack of movement of blood from the wound site. Complete hemostasis was achieved within 10 seconds of the application of the peptide solution in all cases.

A series of pictures was taken of an adult rat in which a portion of the overlying skull was removed and one of the veins of the superior sagittal sinus was transected and then treated with a peptide-containing solution. The initial picture shows the exposed brain and veins of the superior sagittal sinus; the next picture shows the cutting of the vein; the next picture shows bleeding from the ruptured vein; and the final picture shows the same area five seconds after the peptide solution was applied. Complete hemostasis was achieved.

Figure 2:
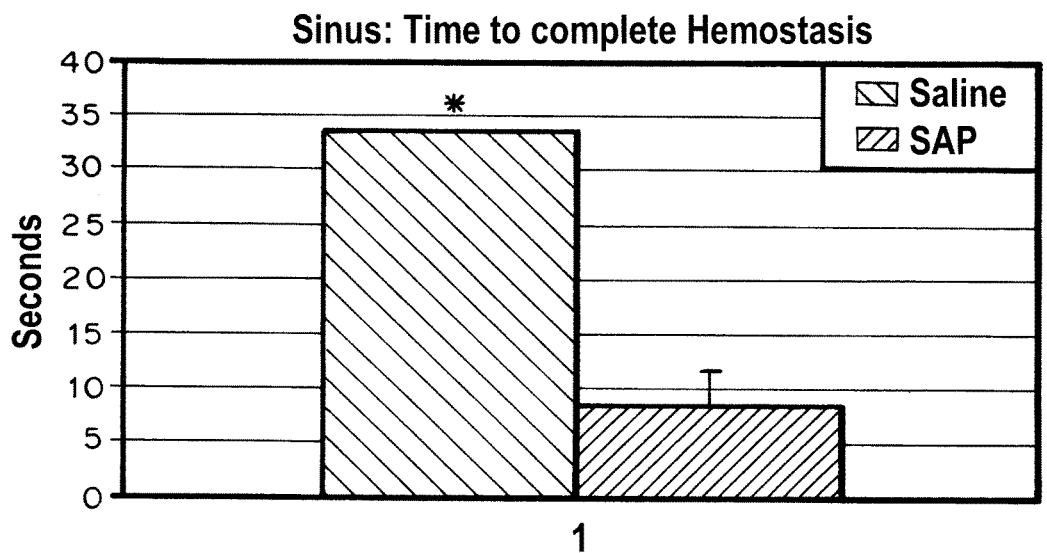
FIG. 2 is a graph comparing the time required to achieve complete hemostasis following treatment with peptide solution (right bar; SAP (self-assembling peptide)) versus saline control (left bar). The study was conducted as described in Example 1. Briefly, adult rodents were anesthetized, a portion of the skull was removed, and a vein of the superior sagittal sinus was transected and then treated with peptide solution or saline.

FIG. 2 is a graph comparing the time required to achieve complete hemostasis following treatment with peptide solution (left bar) versus saline control (right bar) in the situation described immediately above and in Example 1. Durations were measured from the start of application of peptide solution to the completion of hemostasis after transection of the veins leading to the sinus in the brains of adult rats. Each bar shows mean time in seconds for a group of six peptide-treated cases and six control studies. Complete hemostasis was achieved in an average of 8.3 seconds. In the saline controls, cessation of bleeding was never achieved. The * indicates that the saline control experiment was terminated at the indicated time point in order to prevent the animals from bleeding to death.

Similar results have been obtained following complete transection of the superior sagittal sinus. A higher concentration of peptide (e.g., ~3%-4%) was used in the latter experiment in order to achieve hemostasis. The three saline control cases continued to bleed after 20 seconds. In the control animals, the iced saline was removed and the peptide solution was applied, resulting in complete hemostasis almost immediately.

A total of 22 rats and 64 hamsters have been subjected to experiments in which peptide-containing solutions effectively achieved hemostasis within 10 seconds following application to a site intracranial bleeding.

Example 2

Self-Assembling Peptide Material Accelerates Hemostasis Following Femoral Artery Transection The sciatic nerve and the adjacent femoral artery were exposed in adult rats, and the femoral artery was transected. Twelve rats were treated by application of 2011 of a 1% solution of RADA16-I peptide to the site of transection using a glass pipette attached to a syringe body, while controls were treated by applying cold saline to the site of transection. In all treated cases, hemostasis was achieved in less than 10 seconds. The saline control cases continued to bleed until the experiment was terminated at 110 seconds. In these control animals, subsequent replacement of the cold saline with the peptide solution resulted in almost immediate achievement of complete hemostasis.

A series of pictures was taken in an adult rat in which the femoral artery was transected. In the picture taken first, the sciatic nerve and the femoral artery are exposed. The next picture shows the cutting of the artery, and the next picture shows bleeding. After about five seconds, complete hemostasis was observed in the area of a clear gel formed by the assembled peptides in the presence of blood and plasma. The assembled material can be suctioned off the site easily if desired. Complete hemostasis was maintained for the duration of the test (1 hour).

Figure 3:
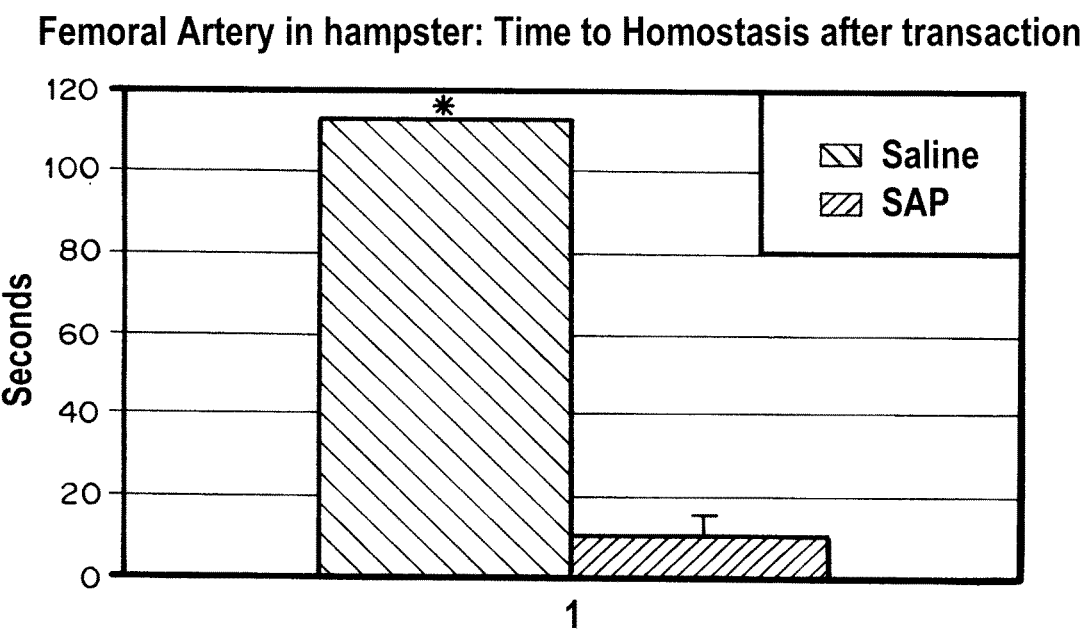
FIG. 3 is a graph of the duration of bleeding in saline-treated controls (left bar) and cases treated with peptide (right), measured from the start of application of peptide solution to the completion of hemostasis following femoral artery transection, as described in Example 2.

FIG. 3 is a graph that illustrates bleeding durations in saline-treated controls (left bar) and in cases treated with peptide (right), measured from the start of application of peptide solution to the completion of hemostasis following femoral artery transection. The bar summarizing a treatment group show an average of time in seconds from six hamster cases in which complete hemostasis was achieved in less than 10 seconds. In the saline controls, hemostasis was never reached. The * indicates that the experiment was terminated so the animals would not bleed to death.

Muscle trauma experiments showed immediate hemostasis after 1-2 cm incisions were made in the muscle on the back of a rat. The spinotrapezius muscles on the back of the rats were exposed and a deep cut was made in the muscle, after which 1% peptide solution (RADA16-I) was applied in the cut. Within 10 seconds, all bleeding had stopped. With the application of iced saline alone, control animals continued to bleed after 20 seconds.

This procedure was duplicated in the muscle of the hind limb (porteocaudalis and musculus tibialis cranialis) and similar results were obtained. Between 1% to 100% peptide (RADA16-I) was applied to limb wounds, and hemostasis was achieved in all cases. However when an artery or vein was transected 2% or higher material was needed to bring about hemostasis. With the application of iced saline alone, control animals continued to bleed after 20 seconds.

Example 3

Self-Assembling Peptide Material Accelerates Hemostasis in Liver

To further demonstrate the ability of peptide-containing structures to halt bleeding of a vessel having relatively low pressure, the intraperitoneal cavity of an adult rat was opened, the liver was exposed, and the lobus sinister lateralis received a rostral to caudal cut completely transecting a portion of the liver. Profuse bleeding ensued. A 1% peptide solution (RADA16-I) was applied to the cut and in its vicinity using a 27 gauge needle and 4 cc syringe. All bleeding stopped within 10 seconds. A series of pictures was obtained. The first shows exposure of the liver; in the second, the liver is separated, and profuse bleeding is evident; and in the third, the two portions of the liver are allowed to come back together, and the bleeding continues. After treating the site with 1% peptide solution (applied topically and in the cut), all bleeding stopped within 10 seconds. A clear area was observed between the two halves of the lobus sinister lateralis. This procedure was repeated several times with the same result.

A similar experiment demonstrated the ability of the peptide structures to halt bleeding of a vessel in the liver having a higher pressure. A series of pictures illustrate the experiment. The first depicts the opened intraperitoneal cavity and exposed liver; in the second, the lobus sinister lateralis received a transverse cut completely transecting a portion of the liver and a major branch of the portal vein; and the third shows profuse bleeding from the site of injury. The cut was treated with 4% peptide solution applied topically and in the cut. All bleeding stopped within 10 seconds. The lower part of the lobus sinister lateralis was pulled downward to show that the peptide structure is in the cut. The site did not bleed even when subjected to this physical stress. Ten minutes later, there was still no bleeding. Thus, application of 4% peptide solution brings about complete hemostasis in a high pressure bleeding environment in less than 10 seconds.

Treatment with a 2% or 3% peptide solution was tested in the same type of experiment and complete hemostasis was also achieved. Treatment with a 1% solution resulted in partial cessation of bleeding. In addition, 30 seconds after treatment the excess peptide structure was wiped away from the injury site and hemostasis was maintained. This procedure was repeated several times with the same result.

In other experiments ¼ of the lobe in the lower right quadrant of the lobus sinistras laterialis was removed, and the margin was treated with a topical application of 2% peptide (RADA16-I) to the site of injury. Bleeding stopped in less than 10 seconds. One minute later the peptide was removed, and complete hemostasis was achieved at the margin of the liver.

Example 4

Self-Assembling Peptide Material

The intestine of an adult rat was perforated with a small cut at the level of the duodenum that resulted in the leakage of gastric fluid into the intraperitoneal cavity. When the site was treated with 2% peptide (RADA16-I) solution all leakage of gastric fluids from the intestine stopped. An additional volume of 2% peptide solution was injected into the duodenum at the level of the injury. This prevented all leakage from the intestine for one hour, the duration of the procedure. In the control cut at the level of the duodenum, the wall of the intestine inverted and gastric fluids continued to leak from the site of injury when left untreated. When the site was treated with peptide solution 15 minutes after the injury, the peptide treatment also stopped all leakage from this injury site. In addition, the treatment stopped the progression of the intestinal wall inversion.

Example 5

Self-Assembling Peptide Material Accelerates Healing of Skin Wounds

To demonstrate the ability of the self-assembling peptides to enhance wound healing, animals were subjected to punch biopsies of the skin and subcutaneous tissue. The regions from which the biopsies were taken were either treated by a single application of self-assembling peptide (RADA16-I) solution or were left untreated. The wounds were left unbandaged. A series of pictures of a 4 mm punch biopsy healing test in which injured animals were treated with the self assembling peptide and compared to matching cases with no treatment illustrates the results. The wounds were photographed on day 0, day 1, day 4, and day 7. The treated wounds healed much faster as evidenced by the contraction of the wound site in all three punches as early as day 1. Treatment with the peptide appeared to speed healing by as much as 5 days in some cases. In all cases, shrinkage of the wound site happened faster in the treated cases.

Example 6

Compositions Containing Lidocaine

RADA16 (modulus I) was mixed with lidocaine (5%) and the mixture was applied to the skin of adult rats before applying a pin prick. When mixed with a self-assembling peptide, the response to pin prick was muted four times longer than the response was muted using lidocaine alone. In addition, we applied solutions of self-assembling peptides and lidocaine to the intestines of two rats while performing intestinal surgery. The solution reduced peristalsis for the duration of the surgery with no apparent side effects to the animals.

The foregoing description is to be understood as being representative only and is not intended to be limiting. Alternative systems and techniques for making and using the compositions and devices of the invention and for practicing the inventive methods will be apparent to one of skill in the art and are intended to be included within the accompanying claims.

What is claimed is:

1. A formulation for making an in vivo barrier structure, comprising:

self-assembling peptides, wherein the self-assembling peptides consist of a sequence of from 8 to 16 amino acid residues conforming to one or more of Formulas I-IV:

$$((Xaa^{neu}\text{-}Xaa^+)_x(Xaa^{neu}\text{-}Xaa^-)_y)_n \quad (I)$$

$$((Xaa^{neu}\text{-}Xaa^-)_x(Xaa^{neu}\text{-}Xaa^+)_y)_n \quad (II)$$

$$((Xaa^+\text{-}Xaa^{neu})_x(Xaa^-Xaa^{neu})_y)_n \quad (III)$$

$$((Xaa^-\text{-}Xaa^{neu})_x(Xaa^+Xaa^{neu})_y)_n \quad (IV)$$

wherein $Xaa^{neu}$ represents alanine or leucine; $Xaa^+$ represents arginine or lysine; $Xaa^-$ represents aspartic acid or glutamic acid; x and y are integers having a value of 1 or 2, or 4, independently; and n is an integer having a value of 1-4, wherein the self-assembling peptides are in an effective concentration to self-assemble upon contact with physiological fluids at an exposed surgical incision site or an exposed wound site of an animal to form a macroscopic structure that inhibits or prevents passage of bodily fluid through the structure, wherein the barrier structure is formed by application of a powder or an aqueous solution of the self-assembling peptides to the exposed surgical incision site or exposed wound site, wherein the solution has a total concentration of less than 5 mM Li+, Na+, K+, and Cs+ ions and a concentration of self-assembling peptides between 1.0% weight to volume and 4.0% weight to volume inclusive.

2. The formulation for making the barrier structure of claim 1, wherein the aqueous solution of the peptides further comprises a pharmaceutically acceptable carrier and/or a non-fibrous agent.

3. The formulation for making the barrier structure of claim 1, further comprising a therapeutic agent, prophylactic agent, diagnostic agent, a pharmaceutically acceptable diluent, filler, or oil.

4. The formulation of claim 3, further comprising anti-inflammatories, vasoconstrictors, anti-infectives, anesthetics, growth factors, cells, organic compounds, biomolecules, coloring agents, vitamins, or metals.

5. The formulation of claim 1, wherein the self-assembling peptides are in an aqueous solution at a concentration of between 1.0% weight to volume to 3.0% weight to volume, inclusive.

6. The formulation of claim 5, wherein the self-assembling peptides are in an aqueous solution at a concentration of between 2.0% weight to volume to 3.0% weight to volume.

7. The formulation of claim 1,
wherein the self-assembling peptides comprise the amino acid sequence RADARADARADARADA (SEQ ID NO: 1).

* * * * *